United States Patent
Nittoli et al.

(10) Patent No.: US 10,526,344 B2
(45) Date of Patent: Jan. 7, 2020

(54) AMINO ACID ACYLATION REAGENTS AND METHODS OF USING THE SAME

(71) Applicant: REGENERON PHARMACEUTICALS, INC., Tarrytown, NY (US)

(72) Inventors: Thomas Nittoli, Pearl River, NY (US); Srinath Thirumalai Rajan, Bensalem, PA (US); Thomas P. Markotan, Newtown, PA (US); Nareshkumar Jain, Ringoes, NJ (US)

(73) Assignee: REGENERON PHARMACEUTICALS, INC., Tarrytown, NY (US)

(*) Notice: Subject to any disclaimer, the term of this patent is extended or adjusted under 35 U.S.C. 154(b) by 0 days.

(21) Appl. No.: 15/554,813

(22) PCT Filed: Mar. 17, 2016

(86) PCT No.: PCT/US2016/022797
§ 371 (c)(1),
(2) Date: Aug. 31, 2017

(87) PCT Pub. No.: WO2016/149464
PCT Pub. Date: Sep. 22, 2016

(65) Prior Publication Data
US 2018/0237456 A1 Aug. 23, 2018

Related U.S. Application Data
(60) Provisional application No. 62/134,065, filed on Mar. 17, 2015.

(51) Int. Cl.
*C07D 263/46* (2006.01)
*C07D 491/04* (2006.01)
*C07D 498/18* (2006.01)

(52) U.S. Cl.
CPC ......... *C07D 498/18* (2013.01); *C07D 263/46* (2013.01)

(58) Field of Classification Search
CPC .................. C07D 263/46; C07D 491/04
USPC .......................... 548/227; 540/462
See application file for complete search history.

(56) References Cited

U.S. PATENT DOCUMENTS

| 4,308,269 A | 12/1981 | Miyashita et al. |
| 4,399,163 A | 8/1983 | Brennan et al. |
| 4,946,942 A | 8/1990 | Fuller et al. |
| 5,663,333 A | 9/1997 | Hodge et al. |
| 6,083,950 A | 7/2000 | Anand et al. |
| 6,333,410 B1 | 12/2001 | Chari et al. |
| 6,562,966 B2 | 5/2003 | Deng et al. |
| 6,872,737 B2 | 3/2005 | Gil et al. |
| 7,598,375 B2 | 10/2009 | Ho et al. |
| 7,649,094 B2 | 1/2010 | Ishii et al. |
| 8,889,855 B2 | 11/2014 | Deng et al. |
| 2006/0167245 A1 | 7/2006 | Widdison et al. |
| 2010/0063109 A1 | 3/2010 | Jordan et al. |
| 2014/0142297 A1 | 5/2014 | Widdison et al. |
| 2014/0178411 A1 | 6/2014 | Qin et al. |
| 2014/0178413 A1 | 6/2014 | Tang et al. |

FOREIGN PATENT DOCUMENTS

| GB | 1 309 993 A | 3/1973 |
| WO | WO 2012/074757 | 6/2012 |
| WO | WO 2014/078566 | 5/2014 |
| WO | WO 2014/094353 | 6/2014 |
| WO | WO 2014/094355 | 6/2014 |
| WO | WO 2014/094527 | 6/2014 |
| WO | WO 2014/140317 A2 | 9/2014 |

OTHER PUBLICATIONS

PubChem—Compound CID 70099182, Create Date Dec. 1, 2012.*
Hang et al., "Asymmetric Synthesis of α-Amino Acids via Cinchona Alkaloid-Catalyzed Kinetic Resolution of Urethane-Protected α-Amino Acid N-Carboxyanhydrides", Journal of the American Chemical Society, 2001, vol. 123, pp. 12696-12697.
Lerchen et al., "Synthesis of 20-O-linked 20(S)-camptothecin glycoconjugates: impact of the side chain of the ester-linked amino acid on epimerization during the acylation reaction and on hydrolytic stability of the final glycoconjugates", Journal fuer Praktische Chemie (DE), 2000, vol. 342, No. 8, pp. 753-760.
Palomo et al., "A β-Lactam Framework as a β-Alanyl Dication Equivalent: New Synthesis of α-Amino Acid N-Carboxy Anhydrides (NCAs) Derived from β-Substituted Alanines", Journal of the Chemical Society, Chemical Communications, 1994, vol. 12, pp. 1505-1507.
Palomo et al., "A β-lactam route to short peptide segments related to Angiotensinconverting enzyme (ACE) inhibitors", Issue in Honor of Prof. Marcial Moreno-Mañas, Arkivoc 2002 (v) 8-16, ISSN 1424-6376, 16 pages.
Palomo et al., "New Synthesis of α-Amino Acid N-Carboxy Anhydrides through Baeyer-Villiger Oxidation of α-Keto β-Lactams", Journal of Organic Chemistry, 1994, vol. 59, pp. 3123-3130.
Database Registry, Chemical Abstracts Service, Columbus, Ohio, US; Aug. 15, 2012, XP002757060, Database accession No. 1391438-82-6, compound with Registry No. 1391438-82-6.
Hans Kricheldorf, "Uber Herstellung and Eigenschaften von 2-Thioxooxazolidonen-(5)", *Chem. Ber*, Jan. 1, 1971, vol. 104, pp. 3156-3167. The second, third, fourth and fifth compounds of Table 2; p. 3166.
International Search Report and Written Opinion in PCT/US2016/022797 dated May 13, 2016, 15 pages.

* cited by examiner

*Primary Examiner* — Venkataraman Balasubramanian
(74) *Attorney, Agent, or Firm* — Squire Patton Boggs (US) LLP

(57) ABSTRACT

Provided herein are compounds useful for appending amino acids to nucleophiles.

14 Claims, No Drawings

AMINO ACID ACYLATION REAGENTS AND METHODS OF USING THE SAME

This application claims priority to, and the benefit of, U.S. Provisional Patent Application No. 62/134,065, entitled AMINO ACID ACYLATION REAGENTS AND METHODS OF USING THE SAME, which was filed Mar. 17, 2015. The contents of this application are herein incorporated by reference in their entirety for all purposes.

TECHNICAL FIELD

The present disclosure relates to amino acid acylation reagents and methods of acylating nucleophiles with the same.

BACKGROUND

α-Amino acids are the basic structural units of proteins and present in the chemical structures of many biologically important compounds. The alpha carbon of α-amino acids, when bonded to a non-hydrogen side chain, is a chiral center. Such amino acids, e.g., alanine, can be one of two stereoisomers, designated L- and D-. An amino acid's stereochemistry can influence a compound's biological properties, including, for example, maytansinoid's properties. Maytansinoids are cytotoxic compounds structurally related to the natural product maytansine. Maytansinoids include C-3 esters of maytansinol, such as C-3 amino acid esters of maytansinol and derivatives of the same. It has been reported that certain C-3 N-methyl-L-alanine esters of maytansinol are more cytotoxic than those of the corresponding D-form. Current methods of synthesizing stereomerically pure C-3 amino acids esters of maytansinol require multiple steps, involve low-yielding reactions, require hard-to-access reagents, and/or require purification steps to remove undesired stereoisomers. Thus, there is need for synthetic methods that efficiently install amino acids, e.g., to provide esters such as C-3 esters of maytansinol, with high stereomeric purity.

SUMMARY

Provided herein are compounds of Formula (I):

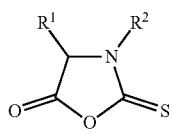

(I)

wherein:
R$^1$ is alkyl, alkenyl, alkynyl, aryl, alkaryl, aralkyl, heteroalkyl, heteroalkenyl, heteroalkynyl, heteroaryl, or an amino acid side chain, and
R$^2$ is a hydrogen atom, alkyl, alkenyl, alkynyl, aryl, alkaryl, aralkyl, heteroalkyl, heteroalkenyl, heteroalkynyl, or heteroaryl.

Furthermore, provided herein are methods of acylating a nucleophile comprising contacting said nucleophile with a compound of Formula (I) in the presence of one or more Lewis acids and one or more bases. In some embodiments, the compound of Formula (I) is a compound of Formula (Ia) or (Ib):

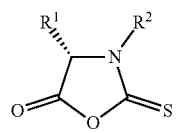

(Ia)

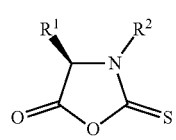

(Ib)

wherein R$^1$ and R$^2$ are as defined above. In certain embodiments, the methods provide an amino acid coupled product that is stereomerically pure.

DETAILED DESCRIPTION

Provided herein are compounds of Formula (I):

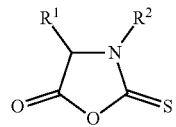

(I)

wherein:
R$^1$ is alkyl, alkenyl, alkynyl, aryl, alkaryl, aralkyl, or an amino acid side chain containing at least one carbon, and
R$^2$ is a hydrogen atom, alkyl, alkenyl, alkynyl, aryl, alkaryl, or aralkyl.

Furthermore, provided herein are processes for acylating a nucleophile comprising contacting said nucleophile with a compound of Formula (I) in the presence of one or more Lewis acids and one or more bases.

Furthermore, provided herein are processes for acylating a nucleophile comprising contacting said nucleophile with a compound of Formula (Ia) or a compound of Formula (Ib) in the presence of one or more Lewis acids and one or more bases.

1. Definitions

As used herein, "alkyl" refers to a monovalent and saturated hydrocarbon radical moiety. Alkyl is optionally substituted and can be linear, branched, or cyclic, i.e., cycloalkyl. Alkyl includes, but is not limited to, those having 1-20 carbon atoms, i.e., $C_{1-20}$ alkyl; 1-12 carbon atoms, i.e., $C_{1-12}$ alkyl; 1-8 carbon atoms, i.e., $C_{1-8}$ alkyl; 1-6 carbon atoms, i.e., $C_{1-6}$ alkyl; and 1-3 carbon atoms, i.e., $C_{1-3}$ alkyl. Examples of alkyl moieties include, but are not limited to methyl, ethyl, n-propyl, i-propyl, n-butyl, s-butyl, t-butyl, i-butyl, a pentyl moiety, a hexyl moiety, cyclopropyl, cyclobutyl, cyclopentyl, and cyclohexyl.

As used herein, "alkenyl" refers to a monovalent hydrocarbon radical moiety containing at least two carbon atoms and one or more non-aromatic carbon-carbon double bonds. Alkenyl is optionally substituted and can be linear, branched, or cyclic. Alkenyl includes, but is not limited to, those having 2-20 carbon atoms, i.e., $C_{2-20}$ alkenyl; 2-12 carbon atoms, i.e., $C_{2-12}$ alkenyl; 2-8 carbon atoms, i.e., $C_{2-8}$ alkenyl; 2-6 carbon atoms, i.e., $C_{2-6}$ alkenyl; and 2-4 carbon atoms, i.e., $C_{2-4}$ alkenyl. Examples of alkenyl moieties include, but are not limited to vinyl, propenyl, butenyl, and cyclohexenyl.

As used herein, "alkynyl" refers to a monovalent hydrocarbon radical moiety containing at least two carbon atoms and one or more carbon-carbon triple bonds. Alkynyl is optionally substituted and can be linear, branched, or cyclic. Alkynyl includes, but is not limited to, those having 2-20 carbon atoms, i.e., $C_{2\text{-}20}$ alkynyl; 2-12 carbon atoms, i.e., $C_{2\text{-}12}$ alkynyl; 2-8 carbon atoms, i.e., $C_{2\text{-}8}$ alkynyl; 2-6 carbon atoms, i.e., $C_{2\text{-}6}$ alkynyl; and 2-4 carbon atoms, i.e., $C_{2\text{-}4}$ alkynyl. Examples of alkynyl moieties include, but are not limited to ethynyl, propynyl, and butynyl.

As use herein, "aryl" refers to a monovalent moiety that is a radical of an aromatic compound wherein the ring atoms are only carbon atoms. Aryl is optionally substituted and can be monocyclic or polycyclic, e.g., bicyclic or tricyclic. Examples of aryl moieties include, but are not limited to those having 6 to 20 ring carbon atoms, i.e., $C_{6\text{-}20}$ aryl; 6 to 15 ring carbon atoms, i.e., $C_{6\text{-}15}$ aryl, and 6 to 10 ring carbon atoms, i.e., $C_{6\text{-}10}$ aryl. Examples of aryl moieties include, but are limited to phenyl, naphthyl, fluorenyl, azulenyl, anthryl, phenanthryl, and pyrenyl.

As used herein, "alkaryl" refers to an aryl that is substituted with at least one alkyl. Alkaryl is optionally substituted.

As used herein, "aralkyl" refers to an alkyl that is substituted with at least one aryl. Aralkyl is optionally substituted.

As used herein, "heteroalkyl" refers to an alkyl in which one or more carbon atoms are replaced by heteroatoms. As used herein, "heteroalkenyl" refers to an alkenyl in which one or more carbon atoms are replaced by heteroatoms. As used herein, "heteroalkynyl" refers to an alkenyl in which one or more carbon atoms are replaced by heteroatoms. Suitable heteroatoms include, but are not limited to, nitrogen, oxygen, and sulfur atoms.

As used herein, "heteroaryl" refers to an aryl in which one or more ring atoms of the aromatic ring are replaced with an oxygen, sulfur, nitrogen, or phosphorus atom.

As used herein, "optionally substituted," when used to describe a monovalent radical moiety, e.g., optionally substituted alkyl, means that such moiety is optionally bonded to one or more substituents. Examples of such substituents include, but are not limited to halo, cyano, nitro, haloalkyl, azido, epoxy, optionally substituted heteroaryl, optionally substituted heterocycloalkyl,

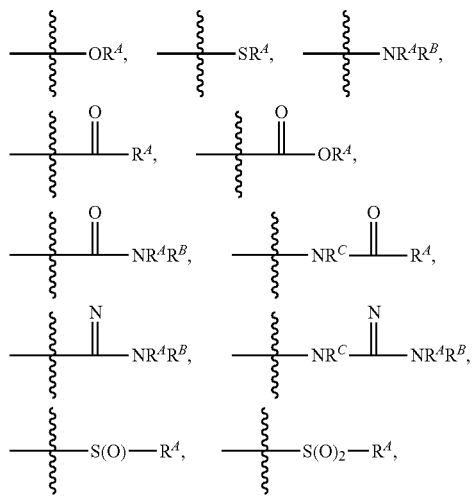

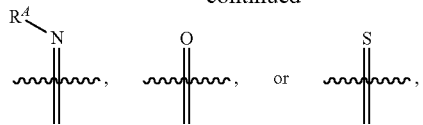

wherein $R^A$, $R^B$, and $R^C$ are, independently at each occurrence, a hydrogen atom, alkyl, alkenyl, alkynyl, aryl, alkaryl, aralkyl, heteroaryl, or heterocycloalkyl, or $R^A$ and $R^B$, together with the atoms to which they are bonded, form a saturated or unsaturated carbocyclic ring, wherein the ring is optionally substituted and wherein one or more ring atoms is optionally replaced with a heteroatom. In some embodiments, $R^A$, $R^B$, and $R^C$ are not hydrogen atoms. In certain embodiments, when a monovalent radical is optionally substituted with an optionally substituted heteroaryl, optionally substituted heterocycloalkyl, or optionally substituted saturated or unsaturated carbocyclic ring, the substituents on the optionally substituted heteroaryl, optionally substituted heterocycloalkyl, or optionally substituted saturated or unsaturated carbocyclic ring, if they are substituted, are not substituted with substituents which are further optionally substituted with additional substituents.

As used herein, "amino acid side chain" refers to a monovalent non-hydrogen substituent that is bonded to an α-carbon of an α-amino acid, including, e.g., natural, non-natural, standard, non-standard, proteinogenic, or non-proteinogenic α-amino acid. Examples of amino acid side chains include, but are not limited to the α-carbon substituent of alanine, valine, leucine, isoleucine, methionine, tryptophan, phenylalanine, proline, serine, threonine, cysteine, tyrosine, asparagine, glutamine, aspartic acid, glutamic acid, lysine, arginine, histidine, and citrulline, and derivatives thereof.

As used herein, "nucleophile" refers to a substance comprising an electron lone pair that reacts with an electrophilic center, thereby forming a covalent cond. Exemplary nucleophiles comprise reactive oxygen, sulfur, and/or nitrogen atoms that form such covalent bond.

As used herein, "Lewis acid" refers to a molecule or ion that accepts an electron lone pair. The Lewis acids used in the methods described herein are those other than protons. Lewis acids include, but are not limited to, non-metal acids, metal acids, hard Lewis acids, and soft Lewis acids. Lewis acids include, but are not limited to, Lewis acids of aluminum, boron, iron, tin, titanium, magnesium, copper, antimony, phosphorus, silver, ytterbium, scandium, nickel, and zinc. Illustrative Lewis acids include, but are not limited to, $AlBr_3$, $AlCl_3$, $BCl_3$, boron trichloride methyl sulfide, $BF_3$, boron trifluoride methyl etherate, boron trifluoride methyl sulfide, boron trifluoride tetrahydrofuran, dicyclohexylboron trifluoromethanesulfonate, iron (III) bromide, iron (III) chloride, tin (IV) chloride, titanium (IV) chloride, titanium (IV) isopropoxide, $Cu(OTf)_2$, $CuCl_2$, $CuBr_2$, zinc chloride, alkylaluminum halides ($R_nAlX_{3-n}$, wherein R is hydrocarbyl; X is a halide selected from F, Cl, Br or I; and n is an integer from 0 to 3), $Zn(OTf)_2$, $Yb(OTf)_3$, $Sc(OTf)_3$, $MgBr_2$, $NiCl_2$, $Sn(OTf)_2$, $Ni(OTf)_2$, and $Mg(OTf)_2$.

As used herein, "base" refers to a molecule or ion that donates an electron lone pair. The bases suitable for the methods described herein are non-nucleophilic, i.e., the bases do not donate an electron pair to and form a bond with electrophiles other than protons.

As used herein, "stereomerically pure" describes a compound wherein, for a given sample of that compound, the indicated stereoisomer is present in a greater extent than other stereoisomers of that compound. In some embodiments, the stereomerically pure compounds described herein comprise 80% or greater, 85% or greater, 90% or greater, 95% or greater, or 97% or greater by weight of one stereoisomer of the compound. The extent of stereomeric purity can be quantified in terms of the compound's enantiomeric excess, i.e., the extent to which an enantiomer is present over the other enantiomer. Compounds that are stereomerically pure have greater than 0% ee, i.e., are not racemic. The term "stereomerically pure" can also be used to describe compounds having two or more stereocenters, wherein a single diastereomer is present to a greater extent than other stereoisomers. This extent can be quantified in terms of the compound's diastereomeric excess. The term "diastereomeric excess" refers to the difference between the mole fraction of the desired single diastereomer as compared to the remaining diastereomers in a composition. Diastereomeric excess is calculated as follows: (amount of single diastereomer)−(amount of other diastereomers)/1. For example, a composition that contains 90% of 1 and 10% of 2, 3, 4, or a mixture thereof has a diastereomeric excess of 80% [(90−10)/1]. A composition that contains 95% of 1 and 5% of 2, 3, 4, or a mixture thereof has a diastereomeric excess of 90% [(95−5)/1]. A composition that contains 99% of 1 and 1% of 2, 3, 4, or a mixture thereof has a diastereomeric excess of 98% [(99−1)/1]. The diastereomeric excess can similarly be calculated for any one of 1, 2, 3, or 4. Methods of determining excess include but are not limited to NMR, chiral HPLC, and optical rotation.

As used herein, "diluent" refers to a non-aqueous liquid organic compound/solvent or mixture of organic compounds/solvents in which the reaction components, e.g., reactants, substrates, and/or reagents are dissolved and/or suspended to facilitate the desired chemical reaction. Diluents include, but are not limited to, low boiling diluents, high boiling diluents, polar aprotic diluents, and non-polar diluents.

As used herein, "appended portion of the nucleophile" refers the structural portion of a referenced nucleophile that is appended to an electrophile following reaction of said nucleophile with said electrophile.

As used herein, "amide synthesis conditions" refers to reaction conditions suitable to effect the formation of an amide, e.g., between the reaction of a carboxylic acid, activated carboxylic acid, or acyl halide with an amine. Suitable conditions include, but are not limited to, those utilizing reagents to effect the reaction between a carboxylic acid an amine, including, but not limited to, dicyclohexylcarbodiimide (DCC), diisopropylcarbodiimide (DIC), (benzotriazol-1-yloxy)tris(dimethylamino)phosphonium hexafluorophosphate (BOP), (benzotriazol-1-yloxy)tripyrrolidinophosphonium hexafluorophosphate (PyBOP), (7-azabenzotriazol-1-yloxy)tripyrrolidinophosphonium hexafluorophosphate (PyAOP), bromotripyrrolidinophosphonium hexafluorophosphate (PyBrOP), O-(benzotriazol-1-yl)-N,N,N',N'-tetramethyluronium hexafluorophosphate (HBTU), O-(benzotriazol-1-yl)-N,N,N',N'-tetramethyluronium tetrafluoroborate (TBTU), 1-[Bis(dimethylamino)methylene]-1H-1,2,3-triazolo[4,5-b]pyridinium 3-oxid hexafluorophosphate (HATU), 2-Ethoxy-1-ethoxycarbonyl-1,2-dihydroquinoline (EEDQ), 1-Ethyl-3-(3-dimethylaminopropyl)carbodiimide (EDC), 2-Chloro-1,3-dimethylimidazolidinium hexafluorophosphate (CIP), 2-chloro-4,6-dimethoxy-1,3,5-triazine (CDMT), and carbonyldiimidazole (CDI).

As used herein, "activated carboxyl" refers to a moiety having the following structure,

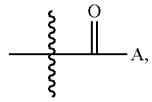

wherein A is a moiety that renders the carbonyl to which it is bonded electrophilic, e.g., reactive to an alcohol, amine, or thiol. Activated carboxyl moieties include, but are not limited to, acid halides, esters, and anhydrides.

As used herein, "amine protecting group" refers to a moiety that is bonded to a nitrogen atom and attenuates the nucleophilic character of said nitrogen atom. Examples of amine protecting groups include, but are not limited to, those disclosed in Peter G. M. Wuts and Theodora W. Greene, "Greene's Protective Groups in Organic Synthesis," 4$^{th}$ ed., 2006, which is incorporated herein by reference in its entirety. Illustrative groups include, but are not limited to BOC, Troc, Cbz, and FMOC.

Certain groups, moieties, substituents, and atoms are depicted with a wiggly line that dissects a bond to indicate the atom through which the groups, moieties, substituents, atoms are bonded. For example, a phenyl group that is substituted with a propyl group depicted as:

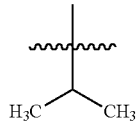

has the following structure:

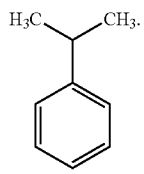

2. Methods

Provided herein are methods of acylating a nucleophile comprising contacting said nucleophile with a compound of Formula (I):

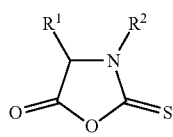

in the presence of one or more Lewis acids and one or more bases, wherein:

$R^1$ is alkyl, alkenyl, alkynyl, aryl, alkaryl, aralkyl, heteroalkyl, heteroalkenyl, heteroalkynyl, heteroaryl, or an amino acid side chain, and $R^2$ is a hydrogen atom, alkyl, alkenyl, alkynyl, aryl, alkaryl, aralkyl, heteroalkyl, heteroalkenyl, heteroalkynyl, or heteroaryl.

In some embodiments, the compound of Formula (I) is a compound of Formula (Ia) or (Ib):

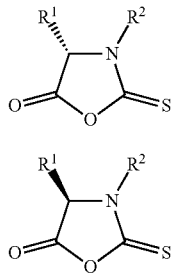

wherein $R^1$ and $R^2$ are as defined above.

In some embodiments, a stereomerically pure compound of Formula (Ia) or stereomerically pure compound of Formula (Ib) is isolated by chiral chromatography. Chiral chromatography can be performed using chiral columns and separation conditions deemed suitable by a practitioner of skill.

Provided herein are also methods of preparing a compound of Formula (II):

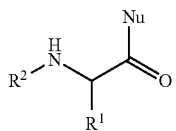

comprising contacting a compound of Formula (I):

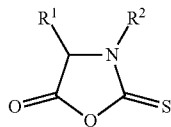

with a nucleophile in the presence of one or more Lewis acids and one or more bases,
wherein:
- $R^1$ is alkyl, alkenyl, alkynyl, aryl, alkaryl, aralkyl, heteroalkyl, heteroalkenyl, heteroalkynyl, heteroaryl, or an amino acid side chain,
- $R^2$ is a hydrogen atom, alkyl, alkenyl, alkynyl, aryl, alkaryl, aralkyl, heteroalkyl, heteroalkenyl, heteroalkynyl, or heteroaryl, and
- Nu is an appended portion of the nucleophile, to form the compound of Formula (II).

Provided herein are also methods of preparing a compound of Formula (IIa):

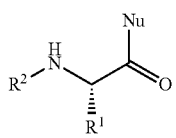

comprising contacting a compound of Formula (Ia):

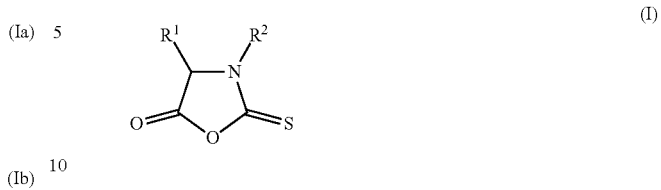

with a nucleophile in the presence of one or more Lewis acids and one or more bases,
wherein:
- $R^1$ is alkyl, alkenyl, alkynyl, aryl, alkaryl, aralkyl, heteroalkyl, heteroalkenyl, heteroalkynyl, heteroaryl, or an amino acid side chain,
- $R^2$ is a hydrogen atom, alkyl, alkenyl, alkynyl, aryl, alkaryl, aralkyl, heteroalkyl, heteroalkenyl, heteroalkynyl, or heteroaryl, and
- Nu is an appended portion of the nucleophile, to form the compound of Formula (IIa). In some embodiments, a stereomerically pure compound of formula (IIa) is isolated by chromatography. The chromatography conditions and methods are any of those deemed suitable by a practitioner of skill.

Provided herein are also methods of preparing a compound of Formula (IIa):

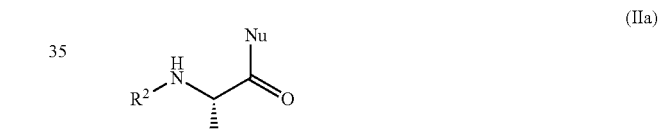

comprising contacting a compound of Formula (Ia):

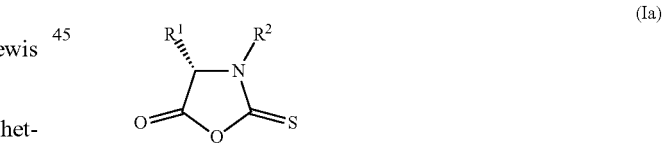

with a nucleophile in the presence of one or more Lewis acids and one or more bases,
wherein:
- $R^1$ is alkyl, alkenyl, alkynyl, aryl, alkaryl, aralkyl, heteroalkyl, heteroalkenyl, heteroalkynyl, heteroaryl, or an amino acid side chain,
- $R^2$ is a hydrogen atom, alkyl, alkenyl, alkynyl, aryl, alkaryl, aralkyl, heteroalkyl, heteroalkenyl, heteroalkynyl, or heteroaryl, and
- Nu is an appended portion of the nucleophile, to form the compound of Formula (IIa), wherein the compound of Formula (IIa) is stereomerically pure.

Provided herein are also methods of preparing compound of Formula (IIb):

comprising contacting a compound of Formula (Ib):

(Ib)

with a nucleophile in the presence of one or more Lewis acids and one or more bases,
wherein:
  R$^1$ is alkyl, alkenyl, alkynyl, aryl, alkaryl, aralkyl, heteroalkyl, heteroalkenyl, heteroalkynyl, heteroaryl, or an amino acid side chain,
  R$^2$ is a hydrogen atom, alkyl, alkenyl, alkynyl, aryl, alkaryl, aralkyl, heteroalkyl, heteroalkenyl, heteroalkynyl, or heteroaryl, and
  Nu is an appended portion of the nucleophile,
to form the compound of Formula (IIb), wherein the compound of Formula II(b) is stereomerically pure.

In some embodiments, the methods are performed in a diluent, wherein said diluent is or comprises one or more polar aprotic solvents.

In some embodiments, the methods are performed at a temperature of 0 to 100° C., 10 to 80° C., 15 to 70° C., 15 to 60° C., 20 to 60° C., or 40 to 60° C. In some embodiments, the methods are performed at a temperature of 45 to 55° C. In some embodiments, the reaction is mixed for at least 2, 4, 6, 8, 10, 12, 24, 36, 48, 60, 72, 84, 96, 108, or 120 hours. In some embodiments, the reaction is performed for 2-50 hours, wherein the reaction is performed initially at room temperature and subsequently at 40 to 60° C. In certain embodiments, the methods are performed at a temperature of 15 to 60° C. for at least 24 hours. In certain embodiments, the methods are performed at a temperature of 20 to 60° C. for at least 24 hours. In some embodiments, the methods are performed at 40 to 60° C. for 4-8 hours in a diluent comprising DMF. In some embodiments, the methods are performed at 50° C. for 6 hours in a diluent comprising DMF.

In some embodiments, the compound of Formula (I), (Ia), or (Ib) is contacted with the nucleophile as described herein under anhydrous conditions. In certain embodiments, the compound of Formula (I), (Ia), or (Ib) is contacted with the nucleophile as described herein in an anhydrous diluent. In certain embodiments, the compound of Formula (I), (Ia), or (Ib) is contacted with the nucleophile in a diluent in the presence of activated molecular sieves.

(a) Compounds of Formula (I)

Provided herein are compounds of Formula (I):

(I)

wherein:
  R$^1$ is alkyl, alkenyl, alkynyl, aryl, alkaryl, aralkyl, heteroalkyl, heteroalkenyl, heteroalkynyl, heteroaryl, or an amino acid side chain, and
  R$^2$ is a hydrogen atom, alkyl, alkenyl, alkynyl, aryl, alkaryl, aralkyl, heteroalkyl, heteroalkenyl, heteroalkynyl, or heteroaryl.

In some embodiments, the compound of Formula (I) is a compound of Formula (Ia) or (Ib):

(Ia)

(Ib)

(i) R$^1$ Moieties

In some embodiments, R$^1$ is $C_{1-20}$ alkyl, $C_{2-20}$ alkenyl, $C_{2-20}$ alkynyl, $C_{7-20}$ alkaryl, $C_{7-20}$ aralkyl, or $C_{6-20}$ aryl. In some embodiments, R$^1$ is $C_{1-6}$ alkyl, $C_{2-6}$ alkenyl, $C_{2-6}$ alkynyl, or $C_{6-10}$ aryl. In some embodiments, R$^1$ is $C_{1-12}$ alkyl. In some embodiments, R$^1$ is $C_{1-6}$ alkyl. In some embodiments R$^1$ is $C_{1-3}$ alkyl. In certain embodiments, the alkyl, alkenyl, alkynyl, or aryl is not substituted. In some embodiments, R$^1$ is methyl.

In some embodiments, R$^1$ is an amino acid side chain. In some embodiments, R$^1$ is:

-continued

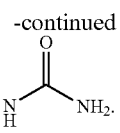

In some embodiments, $R^1$ is

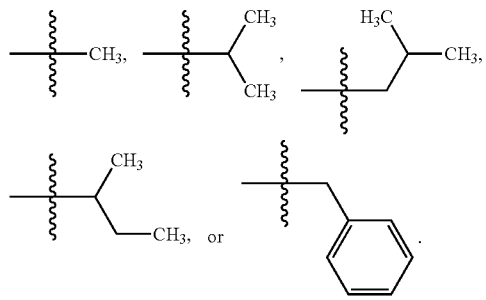

In some embodiments, $R^1$ is

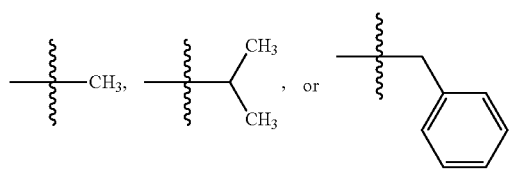

In some embodiments, $R^1$ is an amino acid side chain that does not contain a heteroatom.

(ii) $R^2$ Moieties

In some embodiments, $R^2$ is a hydrogen atom, $C_{1-20}$ alkyl, $C_{2-20}$ alkenyl, $C_{2-20}$ alkynyl, $C_{7-20}$ alkaryl, $C_{7-20}$ aralkyl, or $C_{6-20}$ aryl. In some embodiments, $R^2$ is $C_{1-6}$ alkyl, $C_{2-6}$ alkenyl, $C_{2-6}$ alkynyl, or $C_{6-10}$ aryl. In some embodiments, $R^2$ is not a hydrogen atom. In some embodiments, $R^2$ is $C_{1-12}$ alkyl. In some embodiments, $R^2$ is $C_{1-6}$ alkyl. In some embodiments $R^2$ is $C_{1-3}$ alkyl. In certain embodiments, the alkyl, alkenyl, alkynyl, or aryl is not substituted.

(iv) Amounts

In some embodiments, the compound of Formula (I), (Ia), or (Ib) is present at a reaction concentration of 0.05 to 1.00 M. In some embodiment, the compound of Formula (I), (Ia), or (Ib) is present at 0.05, 0.1, 0.2, 0.3, 0.4, 0.5, 0.6, 0.7, 0.8, 0.9, or 1.0 M. In some embodiments, the compound of Formula (I), (Ia), or (Ib) is present at a concentration of 0.3-0.5 M.

In some embodiments, a stoichiometric amount of the compound of Formula (I), (Ia), or (Ib) is used relative to the nucleophile. In some embodiments, an excess amount of the compound of Formula (I), (Ia), or (Ib) is utilized relative to the nucleophile. In some embodiments, 1.0 to 20 eq., 2.0 to 15 eq., 5 to 15 eq., or 8 to 12 eq. of Lewis acid is utilized relative to nucleophile.

(v) Illustrative Embodiments

In some embodiments:
$R^1$ is an amino acid side chain; and
$R^2$ is a hydrogen atom, $C_{1-20}$ alkyl, $C_{2-20}$ alkenyl, $C_{2-20}$ alkynyl, $C_{7-20}$ alkaryl, $C_{7-20}$ aralkyl, or $C_{6-20}$ aryl.

In some embodiments:
$R^1$ is unsubstituted $C_{1-6}$ alkyl, or benzyl; and
$R^2$ is a hydrogen atom or unsubstituted $C_{1-6}$ alkyl.

In some embodiments:
$R^1$ is unsubstituted $C_{1-6}$ alkyl or benzyl, and
$R^2$ is unsubstituted $C_{1-6}$ alkyl.

In some embodiments:
$R^1$ is $C_{1-20}$ alkyl, $C_{2-20}$ alkenyl, $C_{2-20}$ alkynyl, $C_{7-20}$ alkaryl, $C_{7-20}$ aralkyl, or $C_{6-20}$ aryl, and
$R^2$ is $C_{1-20}$ alkyl, $C_{2-20}$ alkenyl, $C_{2-20}$ alkynyl, $C_{7-20}$ alkaryl, $C_{7-20}$ aralkyl, or $C_{6-20}$ aryl; wherein said alkyl, alkenyl, alkynyl, alkaryl, aralkyl, and aryl of $R^1$ and $R^2$ are not substituted.

In some embodiments:
$R^1$ is $C_{1-6}$ alkyl, $C_{2-6}$ alkenyl, $C_{2-6}$ alkynyl, or $C_{6-10}$ aryl, and
$R^2$ is $C_{1-6}$ alkyl, $C_{2-6}$ alkenyl, $C_{2-6}$ alkynyl, or $C_{6-10}$ aryl; wherein said alkyl, alkenyl, alkynyl, and aryl of $R^1$ and $R^2$ are not substituted.

In some embodiments, $R^1$ and $R^2$ are each, independently, $C_{1-6}$ alkyl.

In some embodiments, the compound of the Formula (I) is a compound of Formula (Ia):

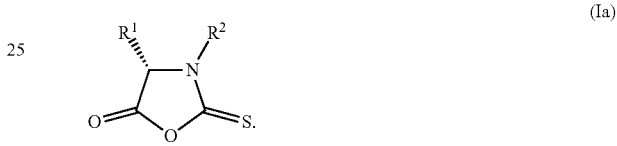

In some embodiments, the compound has the Formula (Ia), wherein:
$R^1$ is unsubstituted $C_{1-6}$ alkyl, or benzyl; and
$R^2$ is unsubstituted $C_{1-6}$ alkyl.

In some embodiments, the compound is:

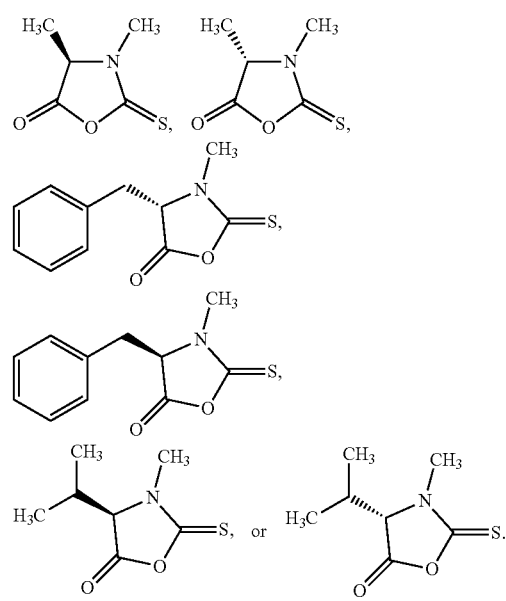

(vi) Preparation of Compounds of Formula (I)

Compounds of Formula (I) are accessible directly in one step from their corresponding amino acid. In some embodiments, compounds of Formula (I) are prepared from by contacting the corresponding amino acid, i.e., compound of Formula (III):

(III)

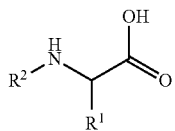

or a salt thereof. For example, compounds of Formula (I) can be prepared by contacting a compound of Formula (III) with 1,1'-thiocarbonyldiimidazole or an O,S-dimethyl ester, e.g., according to U.S. Pat. No. 4,411,925, which is incorporated herein by reference in its entirety. Compounds of Formula (Ia) and (Ib) can be directly obtained from their corresponding chiral L- or D-amino acid.

In some examples, a stereomerically pure compound of Formula (Ia) and (Ib) can isolated using chromatography techniques known to persons having ordinary skill in the art. In some embodiments, a stereomerically pure compound of Formula (Ia) or stereomerically pure compound of Formula (Ib) is obtained by subjecting a mixture of isomers to a chiral column. The chiral column and separation conditions can be any of those deemed suitable by a practitioner of skill. In some examples, the chiral column is a Phenomenex Luc 5 μm Amylose-1 column. In some examples, the chiral column is a Chiral Technologies CHIRALPAKR® 5μ AD-H column.

For example, the compound of Formula (Ia):

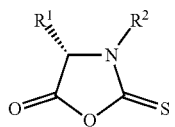

(Ia)

can be prepared in a method comprising contacting a compound of Formula (IIIa):

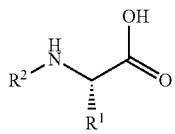

(IIIa)

with 1,1'-thiocarbonyldiimidazole in the presence of one or more bases, wherein:
R$^1$ is alkyl, alkenyl, alkynyl, aryl, alkaryl, aralkyl, heteroalkyl, heteroalkenyl, heteroalkynyl, heteroaryl, or an amino acid side chain, and
R$^2$ is a hydrogen atom, alkyl, alkenyl, alkynyl, aryl, alkaryl, aralkyl, heteroalkyl, heteroalkenyl, heteroalkynyl, or heteroaryl,
to form the compound of Formula (Ia).

Furthermore, the compound of Formula (Ib):

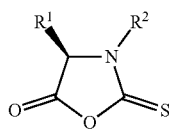

(Ib)

can be prepared in a method comprising contacting a compound of Formula (IIIb):

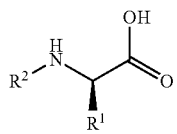

(IIIb)

with 1,1'-thiocarbonyldiimidazole in the presence of one or more bases.
wherein:
R$^1$ is alkyl, alkenyl, alkynyl, aryl, alkaryl, aralkyl, heteroalkyl, heteroalkenyl, heteroalkynyl, heteroaryl, or an amino acid side chain, and
R$^2$ is a hydrogen atom, alkyl, alkenyl, alkynyl, aryl, alkaryl, aralkyl, heteroalkyl, heteroalkenyl, heteroalkynyl, or heteroaryl,
to form the compound of Formula (Ib).

In some embodiments, R$^1$ and R$^2$ are both alkyl. In some embodiments, R$^1$ and R$^2$ are both unsubstituted C$_{1-6}$ alkyl. In some embodiments, R$^1$ and R$^2$ are both methyl.

In some embodiments, a stereomerically pure compound of Formula (Ia) or stereomerically pure compound of Formula (Ib) is obtained by subjecting a compound of Formula (I) to a chiral column. The chiral column and separation conditions can be any of those deemed suitable by a practitioner of skill.

In certain embodiments, the reaction is mixed for 2 to 72 hours. In certain embodiments, the reaction is mixed for at least 2, 4, 6, 8, 10, 12, 24, or 36 hours. In some embodiments, the compounds of Formula (III), (IIIa) or (IIIb) are contacted with the 1,1'-thiocarbonyldiimidazole and one of more bases at −100- to 60° C.; −80 to 30° C.; −50 to 20° C., −20 to 10° C., or 0° C. In some embodiments, the 1,1'-thiocarbonyldiimidazole is added in portions to a mixture of the compound of Formula (III), (IIIa) or (IIIb) and base over 1, 2, 3, 4, 5, 6, 7, 8, 9 or 10 hours. In certain embodiments, the addition is performed at about 0° C. In certain embodiments, the reaction is mixed for an additional 2, 4, 6, 8, 10, 12, or 24 hours after addition of the 1,1'-thiocarbonyldiimidazole. In particular embodiments, the 1,1'-thiocarbonyldiimidazole is added over 4 hours at 0° C. and subsequently warmed to room temperature.

In certain embodiments, a stoichiometric or excess amount of 1,1'-thiocarbonyldiimidazole (with respect to the compound of Formula (III), (IIIa) or (IIIb)) is utilized. In some embodiments, 1.0 to 4.0 eq., 1.05 to 3.0 eq., or 1.1 to 2.0 eq. of 1,1'-thiocarbonyldiimidazole is utilized. In some embodiments, at least 1.1 eq. of 1,1'-thiocarbonyldiimidazole is utilized.

Suitable bases include, but are not limited to, tertiary amine and pyridine bases. In certain embodiments, the base is N,N-diisopropylethylamine (DIPEA), 1,8-diazabicycloundec-7-ene, 2,6-di-tertbutylpyridine, or triethylamine. In certain embodiments, the base is diisopropylethyl amine.

In some embodiments, an excess amount of base is utilized, relative to the compound of Formula (III), (IIIa), or (IIIb). In some embodiments, 1.01 to 20 eq., 1.1 to 10 eq., 1.1 to 5 e.q., 1.5 to 3 eq., 1.5 to 2.5 eq., or 2.0 eq. base is utilized relative to the compound of Formula (III), (IIIa), or (IIIb).

In some embodiments, the compound of Formula (III), (IIIa) or (IIIb) is contacted with the 1,1'-thiocarbonyldiimidazole in the presence of one or more bases in a diluent, wherein the diluent is or comprises one or more polar aprotic solvents. In some embodiments, the diluent is dichloromethane, tetrahydrofuran, dimethylformamide, dimethylsulfoxide, chloroform, or acetone. In some embodiments, the diluent is dichloromethane. In some embodiments, the compound of Formula (III), (IIIa) or (IIIb) is present in the diluent at a concentration of 0.001 M to 0.5 M. In some embodiments, the compound of Formula (III), (IIIa) or (IIIb) is present in the diluent at a concentration of 0.01 to 0.10 M. In some embodiments, the compound of Formula (III), (IIIa) or (IIIb) is present in the diluent at a concentration of 0.02, 0.03, 0.04, 0.05, 0.06, 0.07, 0.08, 0.09, 0.10, 0.11, 0.12, 0.13, 0.14, 0.15, 0.16, 0.17, 0.18, 0.19, 0.2, 0.3, 0.4, 0.5 M.

In some embodiments, the method of preparing the compound of Formula (I), (Ia) or (Ib) further comprises isolating the compound of Formula (I), (Ia) or (Ib) by filtering the reaction mixture through silica gel and eluting the compound of Formula (Ia) or (Ib). In certain embodiments, the eluting is performed with dichloromethane. In certain embodiments, the eluting is performed with a mixture of ethyl acetate and hexanes. In particular embodiments, the eluting is performed using gradient elution with 0-50 percent ethyl acetate in hexanes.

In some embodiments, the compound of Formula (Ia) or (Ib) is obtained in at least 40, at least 50, at least 60, at least 70, at least 80 percent yield, or at least 90 percent yield.

In certain embodiments, the compound of Formula (Ia):

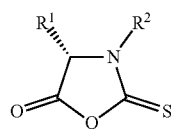

(Ia)

is prepared in a method comprising contacting a compound of Formula (IIIa):

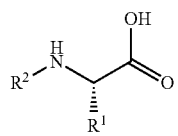

(IIIa)

wherein $R^1$ and $R^2$ is methyl, with 1,1'-thiocarbonyldiimidazole in the presence of a tertiary amine base to form the compound of Formula (Ia).

(b) Nucleophiles

Suitable nucleophiles include, but are not limited to, alcohols, amines, and thiols. In some embodiments, the nucleophile is a compound of formula R—SH or R—OH, wherein R is alkyl, alkenyl, alkynyl, alkaryl, aralkyl, aryl, heteroaryl, or heterocycloalkyl. In some embodiments, the nucleophile is a compound of formula $R^XR^Y$—NH, wherein Rx is alkyl, alkenyl, alkynyl, alkaryl, aralkyl, aryl, heteroaryl, or heterocycloalkyl and $R^Y$ is a hydrogen atom, alkyl, alkenyl, alkynyl, alkaryl, aralkyl, aryl, heteroaryl, or heterocycloalkyl. In certain embodiments, $R^Y$ is a hydrogen atom.

In certain embodiments, the nucleophile is a primary or secondary alcohol. In some embodiments, the nucleophile is a maytansinoid having a C-3 hydroxyl group. In some embodiments, the nucleophile is a compound having the Formula (IV):

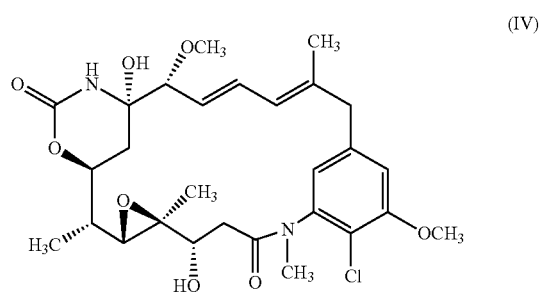 [SMILES: COc1cc2cc(c1Cl)N(C)C(=O)C[C@H](O)[C@]1(C)O[C@H]1[C@H](C)[C@@H]1C[C@@](O)(NC(=O)O1)[C@H](OC)/C=C/C=C(\C)C2]

(IV)

or a stereoisomer, salt, or solvate thereof.

In some embodiments, the compound of Formula (I), (Ia), or (Ib) is contacted with the nucleophile, Lewis acid, and base in a diluent, wherein the concentration of nucleophile in said diluent is 0.005, 0.01, 0.02, 0.03, 0.04, 0.05, 0.06, 0.07, 0.08, 0.09, 0.10, 0.15, 0.20 M.

(c) Lewis Acids

The methods provided herein are performed in the presence of one or more Lewis acids other those generating a proton. In some embodiments, the Lewis acid is $Zn(OTf)_2$, AgOTf, $Sc(OTf)_3$, $Cu(OTf)_2$, $Fe(OTf)_2$, $Ni(OTf)_2$, $Sn(OTf)_2$, $Ni(acac)_2$, $Cu(acac)_2$, $Zn(acac)_2$, $TiCl_4$, and $ZnCl_2$, or $Mg(OTf)_2$. In certain embodiments, the Lewis acid is a Lewis acid of zinc. In some embodiments, the Lewis acid is $Zn(OTf)_2$.

In some embodiments, the compound of Formula (I), (Ia), or (Ib) is contacted with the nucleophile, Lewis acid, and base in a diluent, wherein the concentration of Lewis acid in said diluent is 0.05 to 1 M. In some embodiments, the concentration of the Lewis acid in said diluent is 0.05, 0.06, 0.07, 0.08, 0.09, 0.10, 0.15, 0.20, 0.25, 0.30, 0.35, 0.40, 0.50, 0.60, 0.70, 0.80, 0.90, or 1 M.

In some embodiments, an excess amount of Lewis acid is utilized relative to the nucleophile. In some embodiments, 1.01 to 20 eq., 1.1 to 10 eq., 1.1 to 5.0 eq., or 2.0 to 4.0 eq., or 2.0 to 3.0 eq. of Lewis acid is utilized relative to nucleophile.

(d) Bases

The methods provided herein are performed in the presence of one or more bases that are non-nucleophilic. Illustrative bases include, but are not limited to, sterically hindered amines, e.g., secondary and tertiary amines and pyridines. In some embodiments, the base is a tertiary amine. In some embodiments, the base is triethylamine, tributylamine, diisopropylethylamine, 1,8-diazabicycloundec-7-ene, or 2,6-di-tert-butylpyridine. In certain embodiments, the base is diisopropylethylamine.

In some embodiments, the compound of Formula (I), (Ia), or (Ib) is contacted with the nucleophile, Lewis acid, and base in a diluent, wherein the concentration of base in said diluent is 0.1, 0.15, 0.20, 0.25, 0.30, 0.35, 0.40, 0.45, or 0.50 M.

In some embodiments, an excess amount of base is utilized, relative to the nucleophile. In some embodiments 1.01 to 20 eq., 1.5 to 15 eq., 2 to 10.0 eq., 3.0 to 8.0 eq., or 4.0 to 6.0 eq. of base is utilized relative to the nucleophile.

(e) Diluents

In some embodiments, nucleophile acylation methods described herein are performed in a diluent that is or comprises one or more polar aprotic solvents. Suitable diluents include, but are not limited to, diethyl ether, tetrahydrofuran, N,N-dimethylformamide, 2-methyltetrahydrofuran, 1,4-dioxane, or N,N-dimethylacetamide. In some embodiments, the diluent is N,N-dimethylformamide. In some embodiments, the diluent is or comprises N,N-dimethylformamide or 2-methyltetrahydrofuran. In some embodiments, the diluent comprises N,N-dimethylformamide and 2-methyltetrahydrofuran. In certain embodiments, the diluent comprises N,N-dimethylformamide and 2-methyltetrahydrofuran, wherein the ratio of the volume of N,N-dimethylformamide to the volume of 2-methyltetrahydrofuran is from 1:1 to about 1:10. In certain embodiments, the ratio is 1:2. In some embodiments, the diluent consists of DMF.

(f) Illustrative Embodiments

In some embodiments, the compound of Formula (IIa):

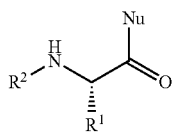

is prepared in a method comprising contacting a compound of Formula (Ia):

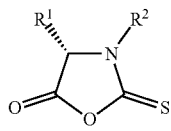

with a nucleophile in the presence of one or more Lewis acids and one or more bases,
wherein:
R$^1$ and R$^2$ are each, independently, C$_{1-20}$ alkyl, C$_{2-20}$ alkenyl, C$_{2-20}$ alkynyl, C$_{7-20}$ alkaryl, C$_{7-20}$ aralkyl, or C$_{6-20}$ aryl, and
Nu is an appended portion of the nucleophile,
to form the compound of Formula (IIa), wherein the compound of Formula (IIa) is stereomerically pure.

In some embodiments, the compound of Formula (IIa):

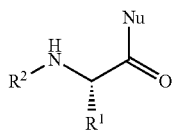

is prepared in a method comprising contacting a compound of Formula (Ia):

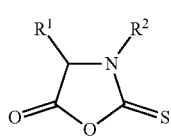

with a nucleophile in the presence of one or more Lewis acids and one or more bases,
wherein:
R$^1$ and R$^2$ are each, independently, C$_{1-20}$ alkyl, C$_{2-20}$ alkenyl, C$_{2-20}$ alkynyl, C$_{7-20}$ alkaryl, C$_{7-20}$ aralkyl, or C$_{6-20}$ aryl, and
Nu is an appended portion of the nucleophile.

In some embodiments, the compound of Formula (IIa):

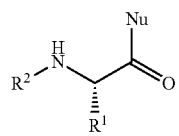

is prepared in a method comprising contacting a compound of Formula (I):

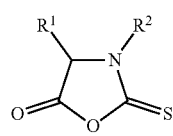

with a nucleophile in the presence of one or more Lewis acids and one or more bases,
wherein:
R$^1$ and R$^2$ are each, independently, C$_{1-20}$ alkyl, C$_{2-20}$ alkenyl, C$_{2-20}$ alkynyl, C$_{7-20}$ alkaryl, C$_{7-20}$ aralkyl, or C$_{6-20}$ aryl, and Nu is an appended portion of the nucleophile,
to form a compound of formula (II):

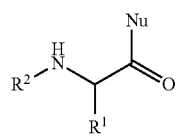

and subsequently isolating the compound of Formula (IIa), wherein the compound of Formula (IIa) is stereomerically pure.

In some embodiments, the compound of Formula (IIa):

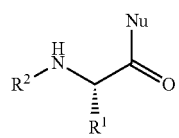

is prepared in a method comprising contacting a compound of Formula (Ia):

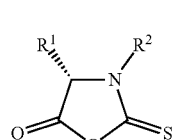

with a nucleophile in the presence of one or more Lewis acids and one or more bases, wherein:

$R^1$ and $R^2$ are each, independently $C_{1-6}$ alkyl, $C_{2-6}$ alkenyl, $C_{2-6}$ alkynyl, or $C_{6-10}$ aryl, and Nu is an appended portion of the nucleophile, to form the compound of Formula (IIa), wherein the compound of Formula (IIa) is stereomerically pure.

In some embodiments, the compound of Formula (IIa):

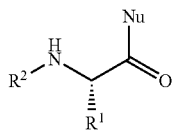
(IIa)

is prepared in a method comprising contacting a compound of Formula (Ia):

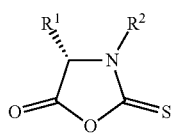
(Ia)

with a nucleophile in the presence of one or more Lewis acids and one or more bases, wherein:

$R^1$ and $R^2$ are each, independently, $C_{1-6}$ alkyl, and

Nu is an appended portion of the nucleophile, to form the compound of Formula (IIa), wherein the compound of Formula (IIa) is stereomerically pure.

In some embodiments, the compound of Formula (IIaa):

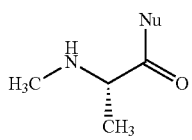
(IIaa)

is prepared in a method comprising contacting a compound of Formula (Iaa):

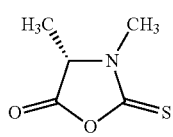
(Iaa)

with a nucleophile in the presence of one or more Lewis acids and one or more bases, wherein Nu is an appended portion of the nucleophile, to form the compound of Formula (IIaa), wherein the compound of Formula (IIaa) is stereomerically pure.

In some embodiments, the compound of Formula (IIa):

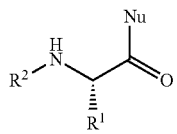
(IIa)

is prepared in a method comprising contacting a compound of Formula (Ia):

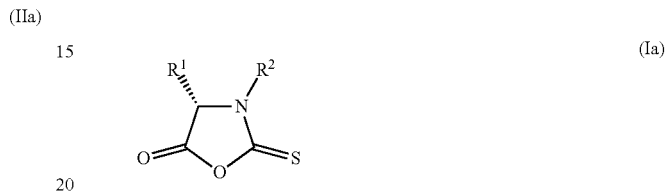
(Ia)

with a nucleophile in the presence of one or more Lewis acids and one or more bases, wherein:

$R^1$ is an amino acid side chain, $R^2$ is $C_{1-20}$ alkyl, $C_{2-20}$ alkenyl, $C_{2-20}$ alkynyl, $C_{7-20}$ alkaryl, $C_{7-20}$ aralkyl, or $C_{6-20}$ aryl, and Nu is an appended portion of the nucleophile, to form the compound of Formula (IIa), wherein the compound of Formula (IIa) is stereomerically pure.

In some embodiments, the compound of Formula (IIa):

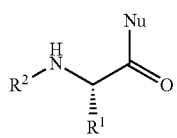
(IIa)

is prepared in a method comprising contacting a compound of Formula (Ia):

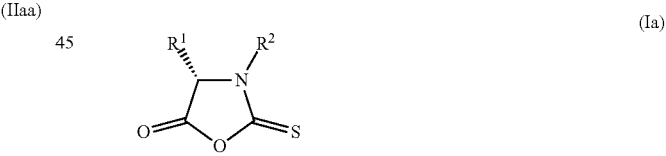
(Ia)

with a nucleophile in the presence of one or more Lewis acids and one or more bases, wherein:

$R^1$ is

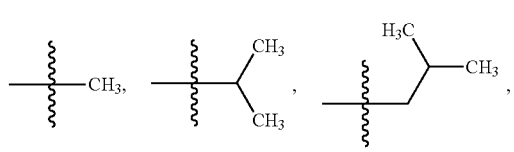

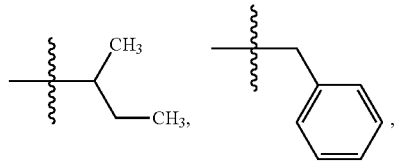

-continued

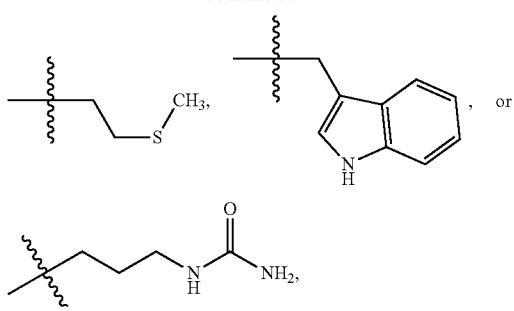
or

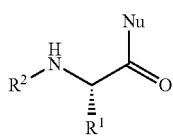

$R^2$ is $C_{1-6}$ alkyl, $C_{2-6}$ alkenyl, $C_{2-6}$ alkynyl, or $C_{6-10}$ aryl, and Nu is an appended portion of the nucleophile, to form the compound of Formula (IIa), wherein the compound of Formula (IIa) is stereomerically pure.

In some embodiments, the compound of Formula (IIa):

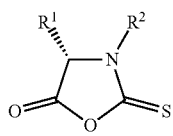 (IIa)

is prepared in a method comprising contacting a compound of Formula (Ia):

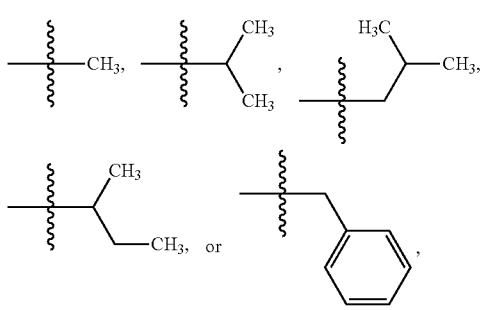 (Ia)

with a nucleophile in the presence of one or more Lewis acids and one or more bases, wherein:

$R^1$ is

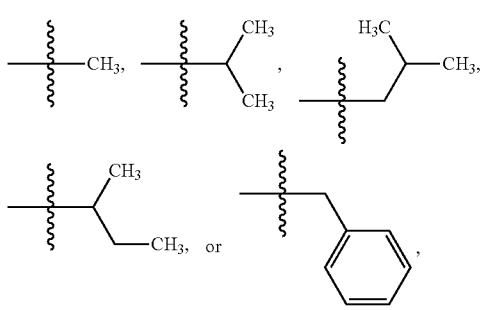

$R^2$ is unsubstituted $C_{1-6}$ alkyl, and

Nu is an appended portion of the nucleophile, to form the compound of Formula (IIa), wherein the compound of Formula (IIa) is stereomerically pure.

In some embodiments, the compound of Formula (IIa):

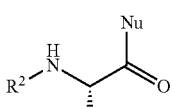 (IIa)

is prepared in a method comprising contacting a compound of Formula (Ia):

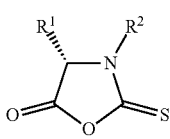 (Ia)

with an alcohol in the presence of one or more Lewis acids and one or more bases, wherein:

$R^1$ and $R^2$ are each, independently, $C_{1-20}$ alkyl, $C_{2-20}$ alkenyl, $C_{2-20}$ alkynyl, $C_{7-20}$ alkaryl, $C_{7-20}$ aralkyl, or $C_{6-20}$ aryl, and Nu is an appended portion of the alcohol, to form the compound of Formula (IIa), wherein the compound of Formula (IIa) is stereomerically pure.

In some embodiments, the compound of Formula (IIa):

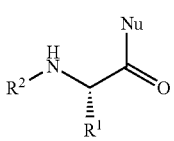 (IIa)

is prepared in a method comprising contacting a compound of Formula (Ia):

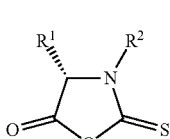 (Ia)

with an alcohol in the presence of one or more Lewis acids and one or more bases, wherein:

$R^1$ and $R^2$ are each, independently $C_{1-6}$ alkyl, $C_{2-6}$ alkenyl, $C_{2-6}$ alkynyl, or $C_{6-10}$ aryl, and Nu is an appended portion of the alcohol, to form the compound of Formula (IIa), wherein the compound of Formula (IIa) is stereomerically pure.

In some embodiments, the compound of Formula (IIa):

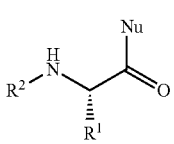 (IIa)

is prepared in a method comprising contacting a compound of Formula (Ia):

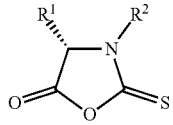
(Ia)

with an alcohol in the presence of one or more Lewis acids and one or more bases,
wherein:
$R^1$ is an amino acid side chain,
$R^2$ is $C_{1-20}$ alkyl, $C_{2-20}$ alkenyl, $C_{2-20}$ alkynyl, $C_{7-20}$ alkaryl, $C_{7-20}$ aralkyl, or $C_{6-20}$ aryl, and
Nu is an appended portion of the alcohol,
to form the compound of Formula (IIa), wherein the compound of Formula (IIa) is stereomerically pure.

In some embodiments, the compound of Formula (IIaaa):

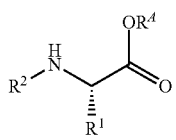
(IIaaa)

is prepared in a method comprising contacting a compound of Formula (Ia):

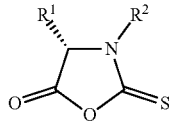
(Ia)

with a nucleophile in the presence of one or more Lewis acids and one or more bases,
wherein:
$R^1$ and $R^2$ are each, independently, alkyl, alkenyl, alkynyl, alkaryl, aralkyl, or aryl,
$R^A$ is alkyl, alkenyl, alkynyl, alkaryl, aralkyl, aryl, heteroalkyl, heteroalkenyl, heteroalkynyl, or heterocycloalkyl, and
the nucleophile is a compound having the formula $R^A$—OH,
to form the compound of Formula (IIaaa), wherein the compound of Formula (IIaaa) is stereomerically pure.

In some embodiments, the compound of Formula (IIa):

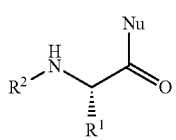
(IIa)

is prepared in a method comprising contacting a compound of Formula (Ia):

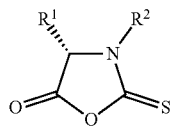
(Ia)

with an alcohol in the presence of:
(i) one or more Lewis acids,
(ii) one or more bases, and
(iii) a diluent comprising one or more polar aprotic solvents,
wherein:
$R^1$ and $R^2$ are each, independently $C_{1-6}$ alkyl, $C_{2-6}$ alkenyl, $C_{2-6}$ alkynyl, or $C_{6-10}$ aryl, and
Nu is an appended portion of the alcohol,
to form the compound of Formula (IIa), wherein the compound of Formula (IIa) is stereomerically pure.

In some embodiments, the compound of Formula (IIa):

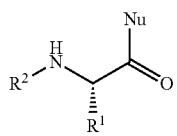
(IIa)

is prepared in a method comprising contacting a compound of Formula (Ia):

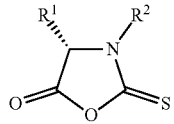
(Ia)

with an alcohol in the presence of
(i) one or more Lewis acids,
(ii) one or more bases, and
(iii) a diluent comprising one or more polar aprotic solvents,
wherein:
$R^1$ is an amino acid side chain,
$R^2$ is $C_{1-20}$ alkyl, $C_{2-20}$ alkenyl, $C_{2-20}$ alkynyl, $C_{7-20}$ alkaryl, $C_{7-20}$ aralkyl, or $C_{6-20}$ aryl, and
Nu is an appended portion of the alcohol,
to form the compound of Formula (IIa), wherein the compound of Formula (IIa) is stereomerically pure.

In some embodiments, the compound of Formula (IIaaa):

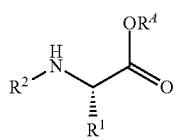
(IIaaa)

is prepared in a method comprising contacting a compound of Formula (Ia):

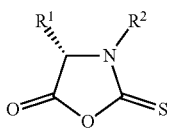

(Ia)

with a nucleophile in the presence of:
 (i) one or more Lewis acids,
 (ii) one or more bases, and
 (iii) a diluent comprising one or more polar aprotic solvents,
wherein:
 $R^1$ and $R^2$ are each, independently, alkyl, alkenyl, alkynyl, alkaryl, aralkyl, or aryl,
 $R^A$ is alkyl, alkenyl, alkynyl, alkaryl, aralkyl, aryl, heteroalkyl, heteroalkenyl, heteroalkynyl, or heterocycloalkyl, and
 the nucleophile is a compound having the formula $R^A$—OH,
to form the compound of Formula (IIaaa), wherein the compound of Formula (IIaaa) is stereomerically pure.

In some embodiments, the compound of Formula (IIa):

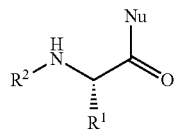

(IIa)

is prepared in a method comprising contacting a compound of Formula (Ia):

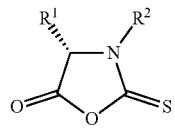

(Ia)

with an alcohol in the presence of one or more Lewis acids and one or more bases,
wherein:
 $R^1$ is an amino acid side chain,
 $R^2$ is $C_{1-20}$ alkyl, $C_{2-20}$ alkenyl, $C_{2-20}$ alkynyl, $C_{7-20}$ alkaryl, $C_{7-20}$ aralkyl, or $C_{6-20}$ aryl, and
 Nu is an appended portion of the alcohol,
to form the compound of Formula (IIa), wherein the compound of Formula (IIa) is stereomerically pure and wherein the alcohol is a maytansinoid having a C-3 hydroxyl group.

In some embodiments, the compound of Formula (IIa):

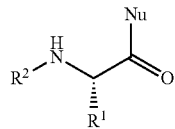

(IIa)

is prepared in a method comprising contacting a compound of Formula (I):

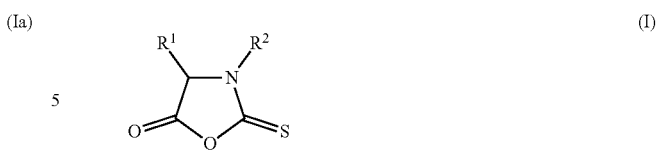

(I)

with an alcohol in the presence of one or more Lewis acids and one or more bases,
wherein:
 $R^1$ is an amino acid side chain,
 $R^2$ is $C_{1-20}$ alkyl, $C_{2-20}$ alkenyl, $C_{2-20}$ alkynyl, $C_{7-20}$ alkaryl, $C_{7-20}$ aralkyl, or $C_{6-20}$ aryl, and
 Nu is an appended portion of the alcohol,
to form the compound of Formula (IIa).

In some embodiments, the compound of Formula (V):

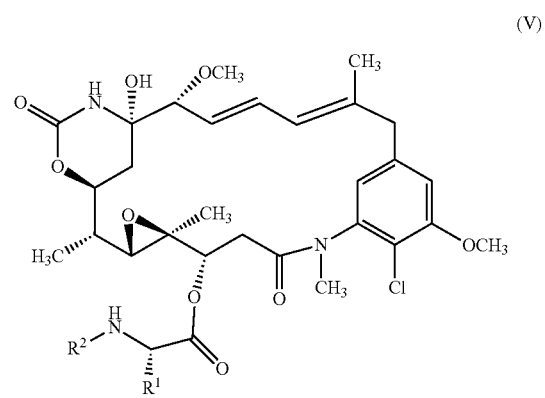

(V)

is prepared in a method comprising contacting a compound of Formula (Ia):

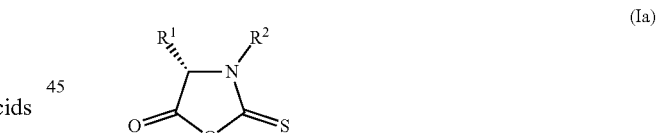

(Ia)

with a compound of Formula (IV):

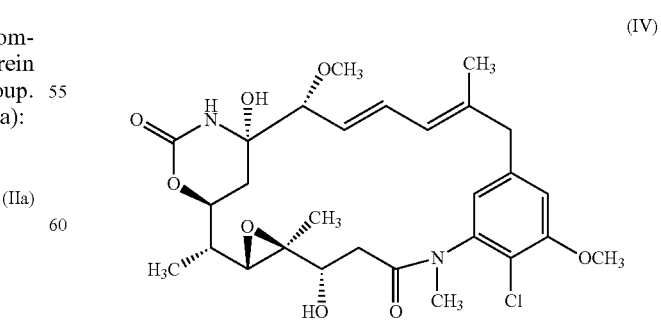

(IV)

in the presence of one or more Lewis acids and one or more bases, wherein:
R[1] is alkyl, alkenyl, alkynyl, aryl, alkaryl, aralkyl, heteroalkyl, heteroalkenyl, heteroalkynyl, heteroaryl, or an amino acid side chain, and
R[2] is alkyl, alkenyl, alkynyl, aryl, alkaryl, aralkyl, heteroalkyl, heteroalkenyl, heteroalkynyl, or heteroaryl,
to form the compound of Formula (V), wherein the compound of Formula (V) is stereomerically pure.

In some embodiments, the compound of Formula (V):

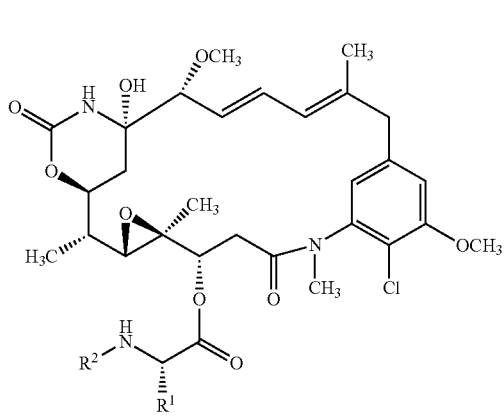

(V)

is prepared in a method comprising contacting a compound of Formula (I):

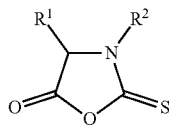

(I)

with a compound of Formula (IV):

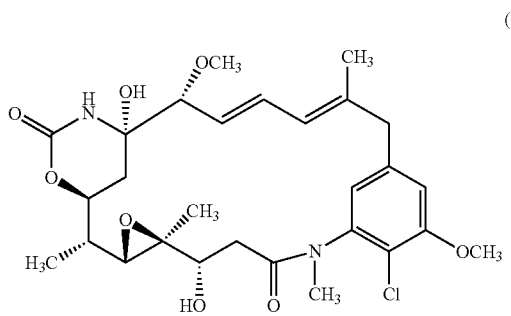

(IV)

in the presence of one or more Lewis acids and one or more bases,
wherein:
R[1] is alkyl, alkenyl, alkynyl, aryl, alkaryl, aralkyl, heteroalkyl, heteroalkenyl, heteroalkynyl, heteroaryl, or an amino acid side chain, and
R[2] is alkyl, alkenyl, alkynyl, aryl, alkaryl, aralkyl, heteroalkyl, heteroalkenyl, heteroalkynyl, or heteroaryl,
to form the compound of Formula (V).

In some embodiments, the compound of Formula (V):

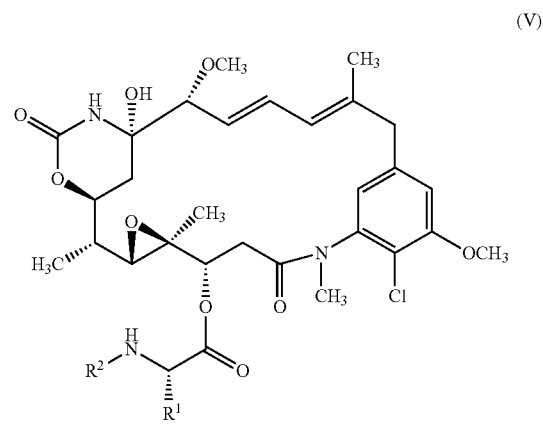

(V)

is prepared in a method comprising contacting a compound of Formula (Ia):

(Ia)

with a compound of Formula (IV):

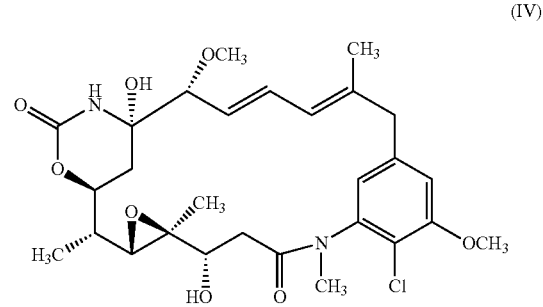 [SMILES: COc1cc2cc(c1Cl)N(C)C(=O)C[C@H](O)[C@]1(C)O[C@H]1[C@H](C)[C@@H]1C[C@@](O)(NC(=O)O1)[C@H](OC)/C=C/C=C(\C)C2]

(IV)

in the presence of one or more Lewis acids and one or more bases,
wherein:
R[1] and R[2] are each, independently, $C_{1-20}$ alkyl, $C_{2-20}$ alkenyl, $C_{2-20}$ alkynyl, $C_{7-20}$ alkaryl, $C_{7-20}$ aralkyl, or $C_{6-20}$ aryl,
to form the compound of Formula (V), wherein the compound of Formula (V) is stereomerically pure.

In some embodiments, the compound of Formula (V):

(V)

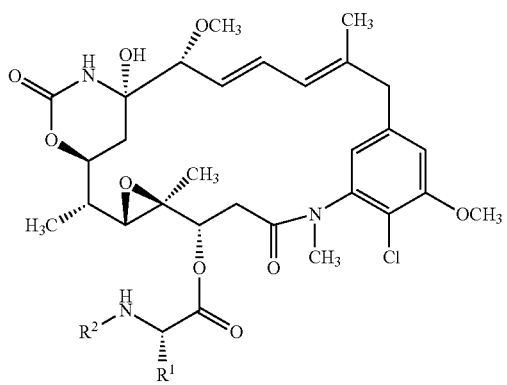

is prepared in a method comprising contacting a compound of Formula (Ia):

(Ia)

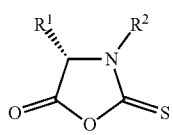

with a compound of Formula (IV):

(IV)

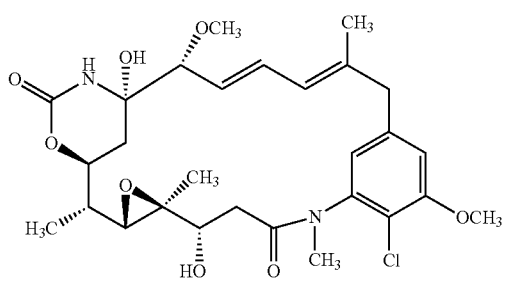

in the presence of one or more Lewis acids and one or more bases,
wherein:
R$^1$ and R$^2$ are each, independently, C$_{1-6}$ alkyl,
to form the compound of Formula (V), wherein the compound of Formula (V) is stereomerically pure.

In some embodiments, the compound of Formula (V):

(V)

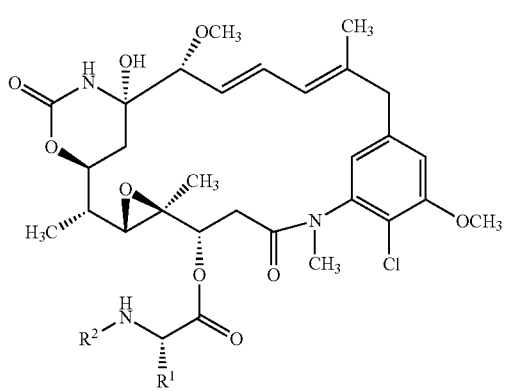

is prepared in a method comprising contacting a compound of Formula (Ia):

(Ia)

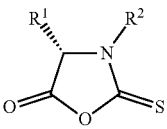

with a compound of Formula (IV):

(IV)

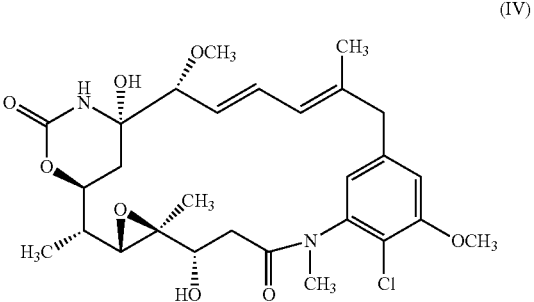 [SMILES: COc1cc2cc(c1Cl)N(C)C(=O)C[C@H](O)[C@]1(C)O[C@H]1[C@H](C)[C@@H]1C[C@@](O)(NC(=O)O1)[C@H](OC)/C=C/C=C(\C)C2]

in the presence of one or more Lewis acids and one or more bases,
wherein:
R$^1$ and R$^2$ are each, independently, unsubstituted C$_{1-6}$ alkyl or benzyl,
to form the compound of Formula (V), wherein the compound of Formula (V) is stereomerically pure.

In some embodiments, the compound of Formula (V):

(V)

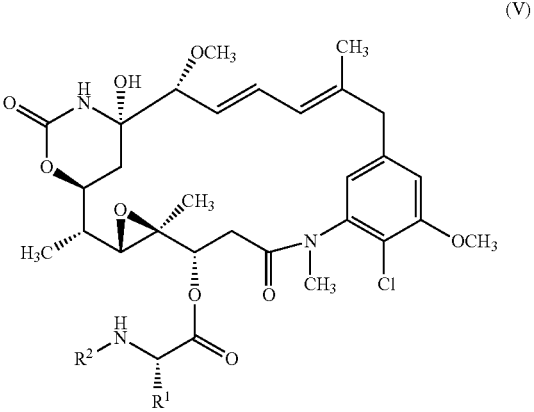

is prepared in a method comprising contacting a compound of Formula (Ia):

(Ia)

with a compound of Formula (IV):

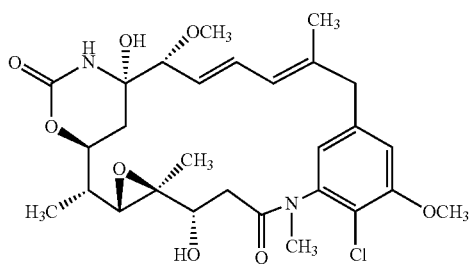

(IV)

in the presence of one or more Lewis acids and one or more bases,
wherein:
R¹ is an amino acid side chain,
R² is $C_{1-20}$ alkyl, $C_{2-20}$ alkenyl, $C_{2-20}$ alkynyl, $C_{7-20}$ alkaryl, $C_{7-20}$ aralkyl, or $C_{6-20}$ aryl,
to form the compound of Formula (V), wherein the compound of Formula (V) is stereomerically pure.

In some embodiments, the compound of Formula (V):

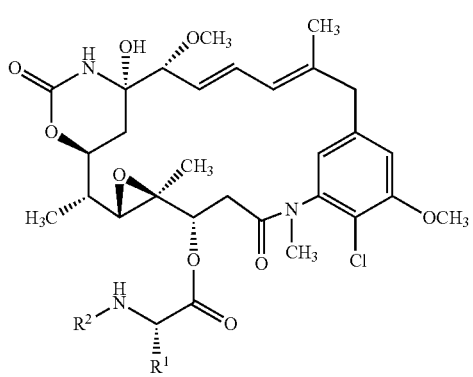

(V)

is prepared in a method comprising contacting a compound of Formula (Ia):

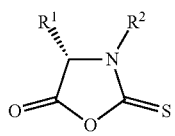

(Ia)

with a compound of Formula (IV):

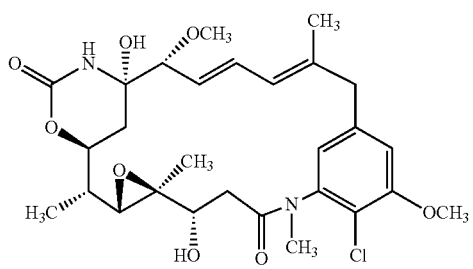

(IV)

in the presence of one or more Lewis acids and one or more bases, wherein:
R¹ is

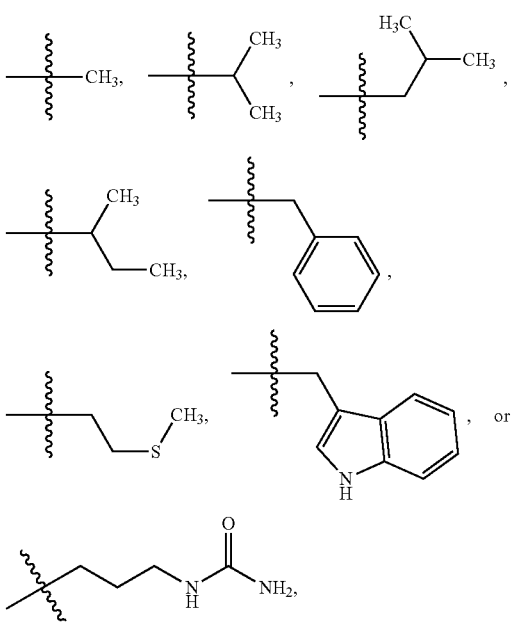

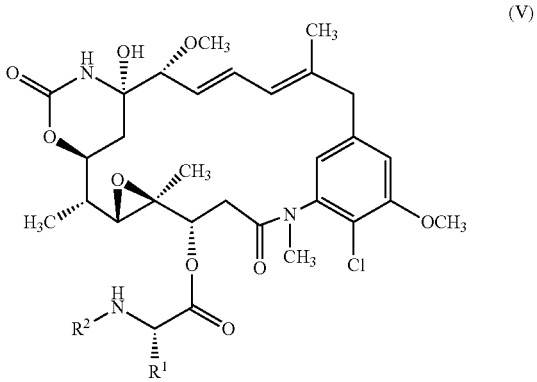

$R^2$ is $C_{1-6}$ alkyl, $C_{2-6}$ alkenyl, $C_{2-6}$ alkynyl, or $C_{6-10}$ aryl,
to form the compound of Formula (V), wherein the compound of Formula (V) is stereomerically pure.

In some embodiments, the compound of Formula (V):

(V)

is prepared in a method comprising contacting a compound of Formula (Ia):

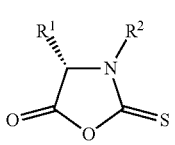

(Ia)

with a compound of Formula (IV):

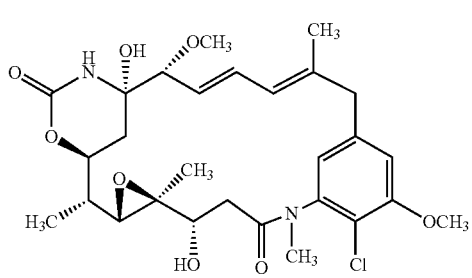
(IV)

in the presence of one or more Lewis acids and one or more bases,
wherein:
R¹ is

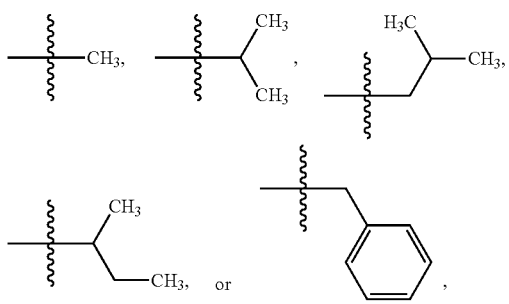

R² is unsubstituted $C_{1-6}$ alkyl,
to form the compound of Formula (V), wherein the compound of Formula (V) is stereomerically pure.

In some embodiments, the compound of Formula (Va):

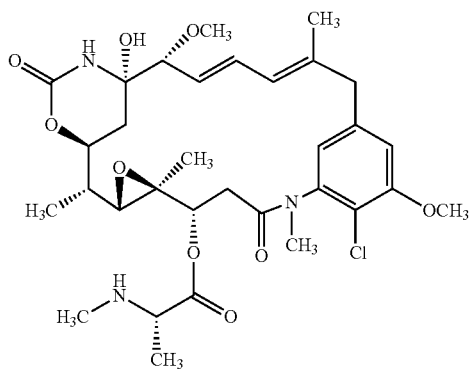
(Va)

is prepared in a method comprising contacting a compound of Formula (Iaa):

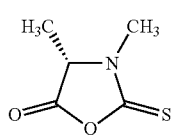
(Iaa)

with a compound of Formula (IV):

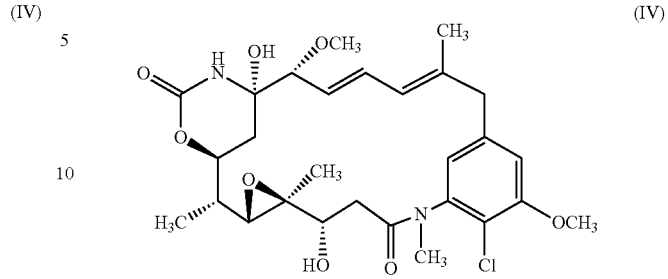
(IV)

in the presence of one or more Lewis acids and one or more bases,
to form the compound of Formula (Va), wherein the compound of Formula (Va) is stereomerically pure.

In some embodiments, the compound of Formula (Va):

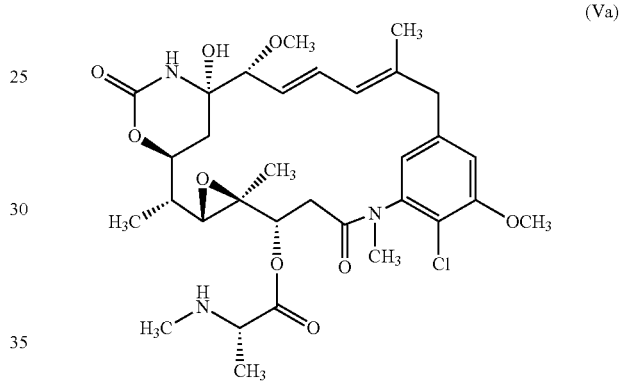
(Va)

is prepared in a method comprising contacting a compound of Formula 2:

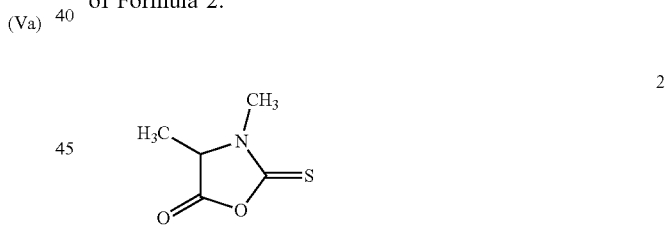
2 with a compound of Formula (IV):

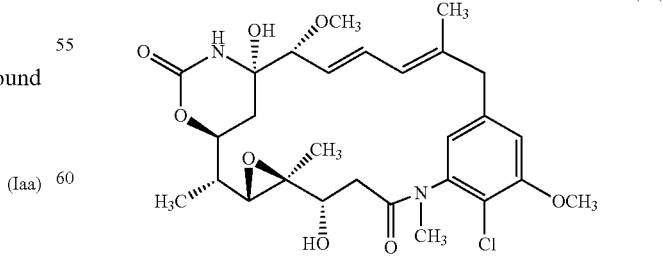
(IV)

in the presence of one or more Lewis acids and one or more bases,
to form the compound of Formula (Va).

In some embodiments, the compound of Formula (Va):

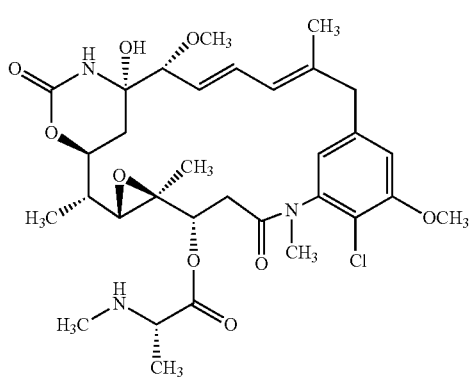

is prepared in a method comprising contacting a compound of Formula (Iaa):

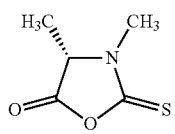

with a compound of Formula (IV):

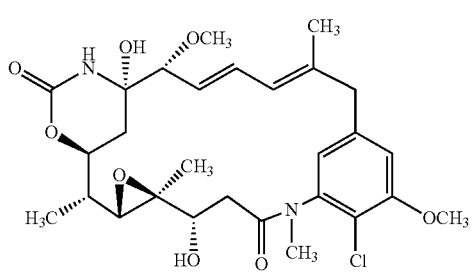

in the presence of:
(i) one or more Lewis acids,
(ii) one or more bases, and
(ii) a diluent comprising one or more polar aprotic solvents,
to form the compound of Formula (Va), wherein the compound of Formula (Va) is stereomerically pure.

In some embodiments, the compound of Formula (Va):

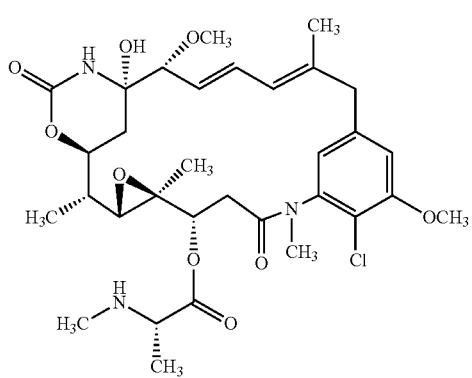

is prepared in a method comprising contacting a compound of Formula (2):

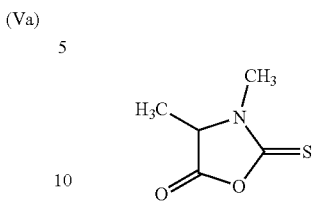

with a compound of Formula (IV):

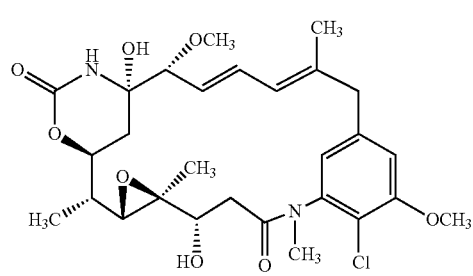

in the presence of:
(i) one or more Lewis acids,
(ii) one or more bases, and
(ii) a diluent comprising one or more polar aprotic solvents,
to form the compound of Formula (Va).

In some embodiments, the compound of Formula (Va):

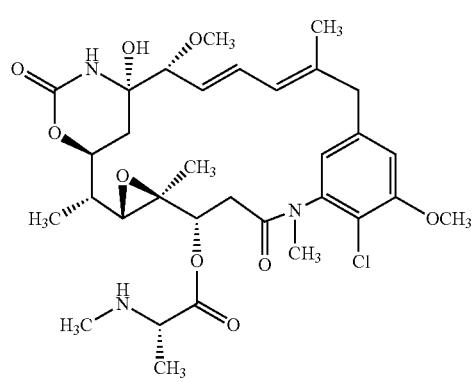

is prepared in a method comprising contacting a compound of Formula (Iaa):

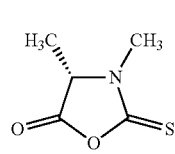

with a compound of Formula (IV):

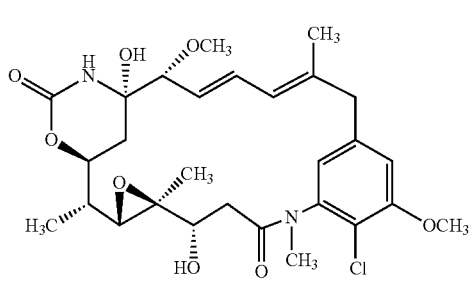
(IV)

in the presence of:
(i) one or more Lewis acids, wherein the one or more Lewis acids is selected from the group consisting of Zn(OTf)$_2$, Ag(OTf)$_2$, Sc(OTf)$_2$, Cu(OTf)$_2$, Fe(OTf)$_2$, Ni(OTf)$_2$, Mg(OTf)$_2$, Ni(acac)$_2$, Cu(acac)$_2$, Zn(acac)$_2$, TiCl$_4$, and ZnCl$_2$, and BF$_3$*Et$_2$O
(ii) one or more bases, wherein the one or more bases is selected from the group consisting of triethylamine, tributylamine, diisopropylethylamine, 1,8-diazabicycloundec-7-ene, and 2,6-di-tert-butylpyridine and
(ii) a diluent comprising one or more polar aprotic solvents, wherein the one of more polar aprotic solvents is selected from the group consisting of diethyl ether, tetrahydrofuran, N,N-dimethylformamide, 2-methyl-tetrahydrofuran, 1,4-dioxane, and N,N-dimethylacetamide, to form the compound of Formula (Va), wherein the compound of Formula (Va) is stereomerically pure.

In some embodiments, the compound of Formula (Va):

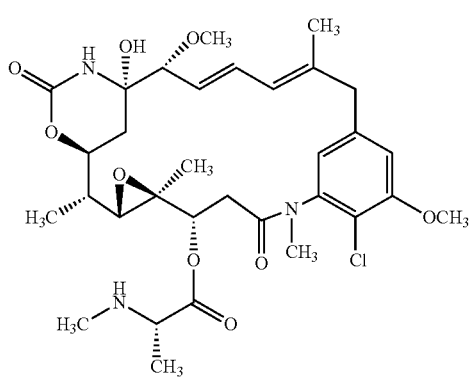
(Va)

is prepared in a method comprising contacting a compound of Formula (Iaa):

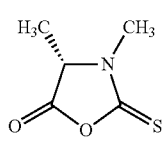
(Iaa)

with a compound of Formula (IV):

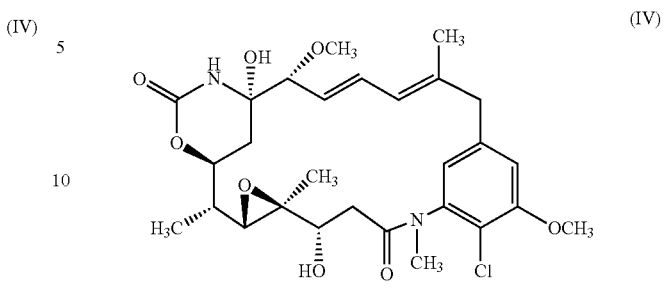
(IV)

in the presence of zinc triflate, N,N,-diisopropylethylamine, dimethylformamide, and 2-methyl-tetrahydrofuran to form the compound of Formula (Va), wherein the compound of Formula (Va) is stereomerically pure.

In some embodiments, the compound of Formula (Va):

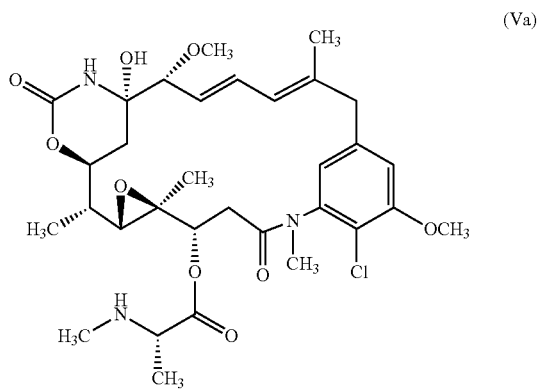 [SMILES: CN[C@@H](C)C(=O)O[C@H]1CC(=O)N(C)c2cc(cc(OC)c2Cl)C/C(C)=C/C=C/[C@@H](OC)[C@@]2(O)C[C@H](OC(=O)N2)[C@@H](C)[C@@H]2O[C@@]12C]
(Va)

is prepared in a method comprising contacting a compound of Formula 2:

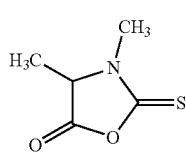
2 with a compound of Formula (IV):

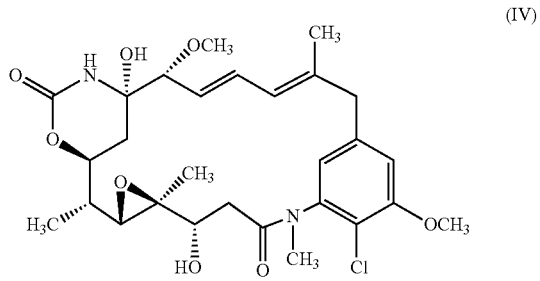 [SMILES: COc1cc2cc(c1Cl)N(C)C(=O)C[C@H](O)[C@]1(C)O[C@H]1[C@H](C)[C@@H]1C[C@@](O)(NC(=O)O1)[C@H](OC)/C=C/C=C(\C)C2]
(IV)

in the presence of zinc triflate, N,N,-diisopropylethylamine, dimethylformamide, and 2-methyl-tetrahydrofuran to form the compound of Formula (Va).

In some embodiments of the acylation reactions described herein, the nucleophile is maytansinol, wherein unreacted maytansinol is recovered. In some embodiments, said unreacted maytansinol is recovered and re-subjected to the acylation conditions described herein.

Provided herein are also methods of preparing a compound of Formula (VI):

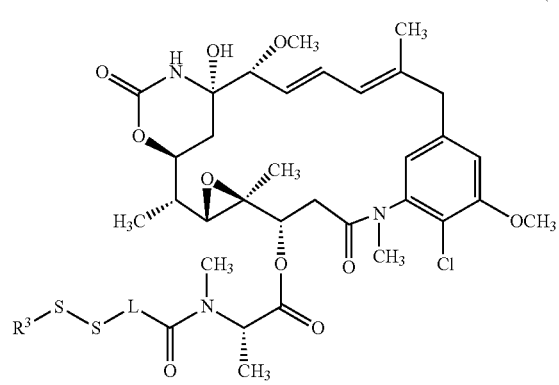
(VI)

comprising contacting a compound of Formula (Va)

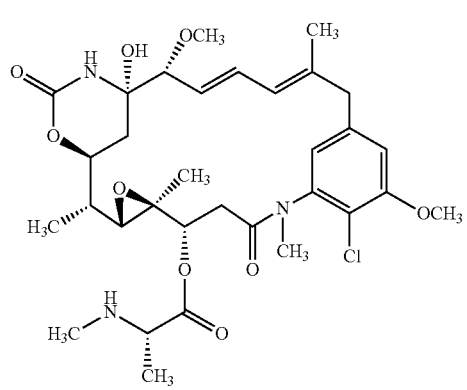
(Va)

with a compound of Formula (VII):

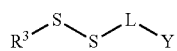
(VII)

under amide synthesis conditions,
wherein:
R[1] is alkyl, alkenyl, alkynyl, aryl, alkaryl, aralkyl, heteroalkyl, heteroalkenyl, heteroalkynyl, heteroaryl, or an amino acid side chain,
R[2] is alkyl, alkenyl, alkynyl, aryl, alkaryl, aralkyl, heteroalkyl, heteroalkenyl, heteroalkynyl, or heteroaryl,
R[3] is methyl,
L is ethylene, n-propylene,

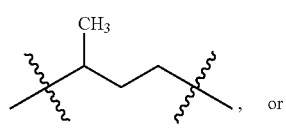
, or

-continued

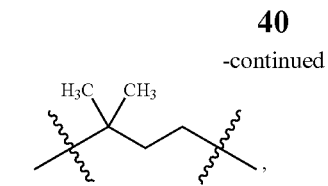
,

Y is carboxyl or activated carboxyl, and
wherein the compound of Formula (V) is prepared in a method comprising contacting a compound of Formula (Iaa):

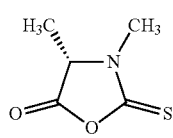
(Iaa)

with a compound of Formula (IV):

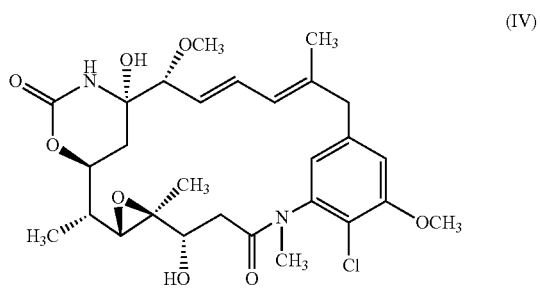 [SMILES: COc1cc2cc(c1Cl)N(C)C(=O)C[C@H](O)[C@]1(C)O[C@H]1[C@H](C)[C@@H]1C[C@@](O)(NC(=O)O1)[C@H](OC)/C=C/C=C(\C)C2]
(IV)

in the presence of one or more Lewis acids and one or more bases.

In some embodiments, the compound of Formula (VI) is

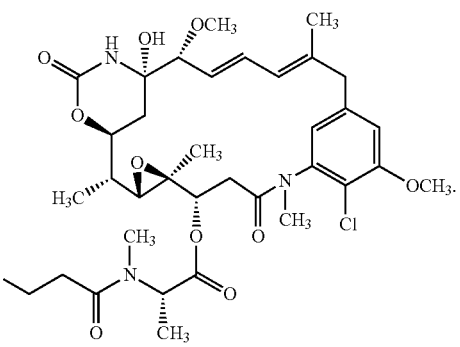

Provided herein are also methods of preparing a compound of Formula (VIII):

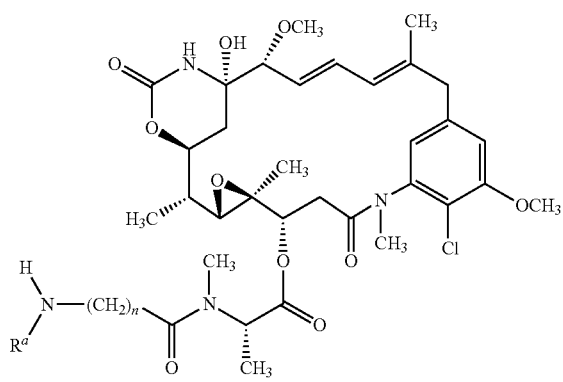

(VIII)

wherein $R^a$ is a hydrogen atom or methyl and n is 2 or 3, comprising the steps of
(i) contacting a compound of Formula (Va)

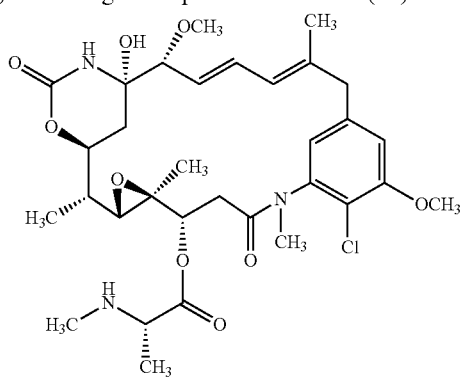

(Va)

with a compound of Formula (IX)

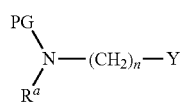

(IX)

wherein PG is an amine protecting group, Y is carboxyl or activated carboxyl, and $R^A$ and n are as defined above,
under amide synthesis conditions to form a compound of Formula (X):

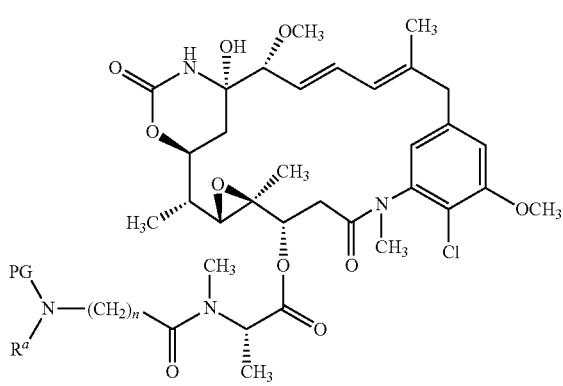

(X)

wherein PG, $R^A$, and n are as defined above, and
(ii) removing the amine protecting group of the compound of Formula (X) to provide the compound of Formula (VIII), wherein the compound of Formula (Va) is obtain by is prepared in a method comprising contacting a compound of Formula (Iaa):

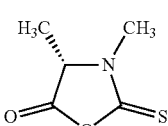

(Iaa)

with a compound of Formula (IV):

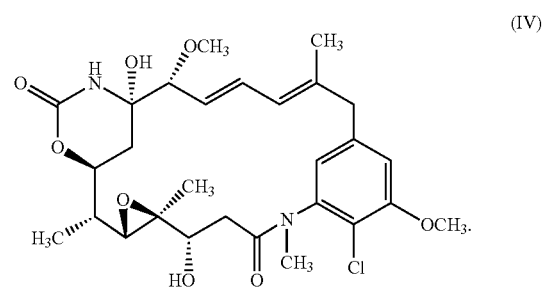 [SMILES: COc1cc2cc(c1Cl)N(C)C(=O)C[C@H](O)[C@]1(C)O[C@H]1[C@H](C)[C@@H]1C[C@@](O)(NC(=O)O1)[C@H](OC)/C=C/C=C(\C)C2]

(IV)

in the presence of one or more Lewis acids and one or more bases.

In some embodiments, the compound of Formula (VIII) is:

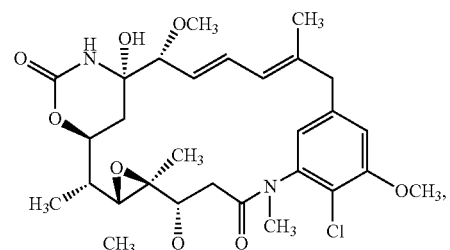

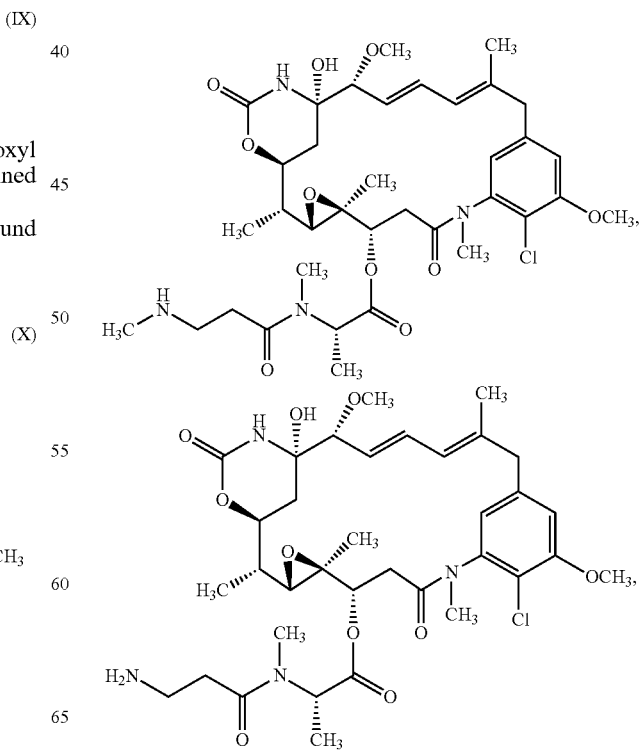

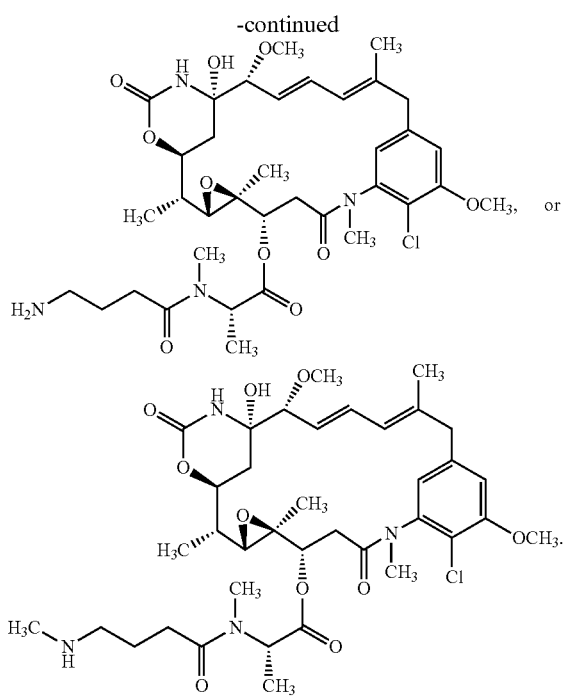

Provided herein are also methods of preparing a compound of Formula (XI):

wherein
Z' is comprising the steps of
(i) contacting the compound of Formula (Va):

with a compound of Formula (XII):

PG-Z'—Y    (XII)

wherein:
Z' is as defined above,
PG is an amine protecting group capping the nitrogen of Z', and
Y is carboxyl or activated carboxyl,
under amide synthesis conditions to form a compound of Formula (XIII):

wherein PG and Z' is as defined above, and
(ii) removing the amine protecting group of the compound of Formula (XIII) to form the compound of Formula (XI),
wherein the compound of Formula (Va) is prepared in a method comprising contacting a compound of Formula (Iaa):

with a compound of Formula (IV):

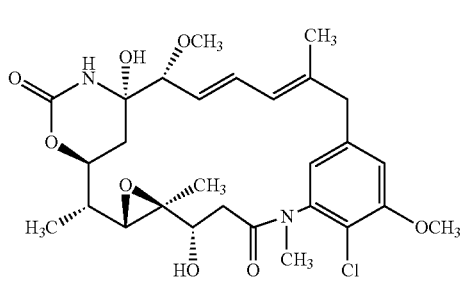

in the presence of one or more Lewis acids and one or more bases.

In some embodiments, the compound of Formula (XI) is:

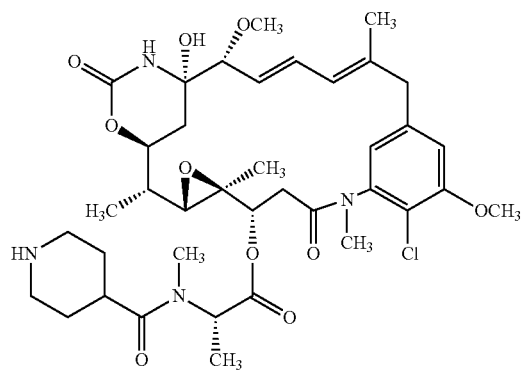

or

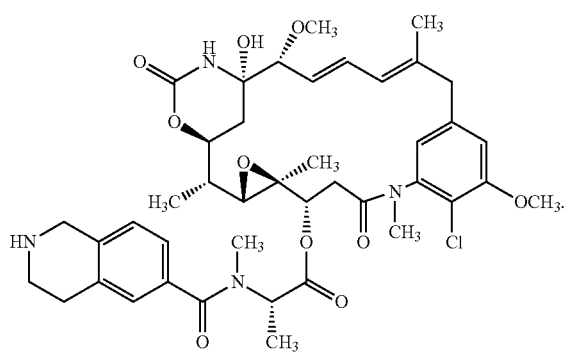

3. EXAMPLES

Certain embodiments of the invention are illustrated by the following non-limiting examples.

Proton NMR spectra were acquired on a Varian Inova 300 MHz or Bruker 500 MHz instrument, while mass spectra were collected on an Agilent 1100 or 1200 series LC/MSD with electrospray ionization source and quadrupole or ion trap analyzer. Solvents were dried over activated molecular sieves. Lewis acids were dried in a vacuum desiccator over phosphorus pentoxide.

Example 1

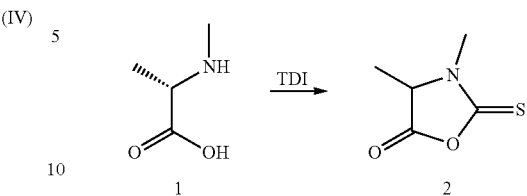

3,4-Dimethyl-2-thioxo-oxazolidin-5-one (compound 2): To a 1 L 3-neck round bottom flask equipped with a magnetic stirrer, condenser, thermocouple and nitrogen inlet was charged N-methyl-L-alanine (compound 1, 1.0 g; 9.70 mmol) and DCM (600 mL) followed by DIEA (3.7 mL; 21.4 mmol; 2.2 eq). This solution was chilled to 0° C. via an ice bath. The 1,1'-thiocarbonyldiimidazole (TDI, 1.82 g; 10.2 mmol, 1.05 eq) was added to the reaction mixture in portions over 4 hours. The reaction was stirred in an ice bath and slowly warmed to room temperature overnight. The reaction was filtered through a plug of silica gel with DCM then eluted with ethyl acetate/hexanes. The filtrate was concentrated to dryness giving the title compound as an orange oil (1.29 g, 91% yield). MS (ESI, pos.): calc'd for $C_5H_7NO_2S$, 145.18; found 146.00 (M+H), 168.2 (M+Na). $^1$H-NMR (300 MHz, $CDCl_3$): δ 4.02-4.14 (q, 1H), 3.05 (s, 3H), 1.52-1.50 (d, 3H). $^{13}$C-NMR (300 MHz, $CDCl_3$): δ 198.1, 164.2, 67.7, 29.5, 16.7.

3,4-Dimethyl-2-thioxo-oxazolidin-5-one (compound 2, alternative Preparation): To a 1 L 3-neck round bottom flask equipped with a magnetic stirrer, addition/dropping funnel, thermocouple and nitrogen inlet was charged N-methyl-L-alanine (compound 1, 2.0 g; 19.40 mmol) and DCM (400 mL) followed by DIEA (7.4 mL; 42.8 mmol; 2.2 eq). This solution was stirred for 5-10 min at room temperature and then chilled to 0° C. via an ice bath. To the ice cold solution, a solution of 1,1'-thiocarbonyldiimidazole (TDI, 3.45 g; 19.40 mmol, 1.0 eq) in DCM (200 mL) was added to the reaction mixture dropwise via addition funnel over a period of 5 hours at 0° C. The reaction mixture was pale brown in color during the addition of TDI and was allowed to warm slowly to room temperature overnight. The reaction was filtered through a plug of silica gel and washed with DCM. The combined filtrate was evaporated to give a yellow colored oil, which was then purified by normal phase column chromatography eluting with a gradient of EtOAc (0% v/v to 70% v/v) in hexanes. Fractions that contained the desired product were then pooled and concentrated to dryness to give the title compound as an orange oil (2.3 g, 82% yield).

Example 2

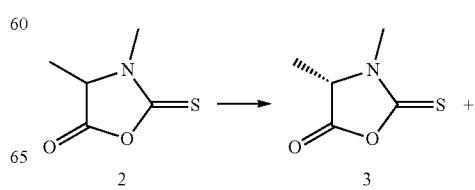

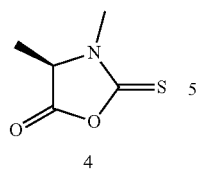

(S) 3,4-Dimethyl-2-thioxo-oxazolidin-5-one (3) and
(R) 3,4-Dimethyl-2-thioxo-oxazolidin-5-one (4)

Method 1: The product 2 from Example 1 was injected onto a 4.6×100 mm Phenomenex Lux 5 μm Amylose-1 (Torrence, Calif.) column and eluted with a 80:20 mixture of hexanes:ethanol with 0.1% v/v TFA mobile phase over 10 min at 1 ml/min with UV detection at 230 nm. The retention times were 4.1 min and 5.4 min.

Method 2: The product 2 from Example 1 was injected onto a 30×250 mm Chiral Technologies CHIRALPAKR® 5 μm AD-H (West Chester, Pa.) and eluted with a 80:20 mixture of hexanes:ethanol with 0.1% v/v TFA mobile phase at 40.0 mL/min over 15 min with UV detection at 230 nm. The retention times were 10.0 min $[\alpha]^{20}_{589\ nm}$=−0.1 (c=0.65, CDCl$_3$) and 13.2 min $[\alpha]^{20}_{589\ nm}$=+0.1 (c=0.4, CDCl$_3$).

(−) 3,4-Dimethyl-2-thioxo-oxazolidin-5-one): MS (ESI, pos.): calc'd for $C_5H_7NO_2S$, 145.18; found 146.00 (M+H). $^1$H-NMR (300 MHz, CDCl$_3$): δ 4.02-4.14 (q, 1H), 3.05 (s, 3H), 1.52-1.50 (d, 3H).

(+) 3,4-Dimethyl-2-thioxo-oxazolidin-5-one: MS (ESI, pos.): calc'd for $C_5H_7NO_2S$, 145.18; found 146.00 (M+H). $^1$H-NMR (300 MHz, CDCl$_3$): δ 4.02-4.14 (q, 1H), 3.05 (s, 3H), 1.52-1.50 (d, 3H).

Example 3

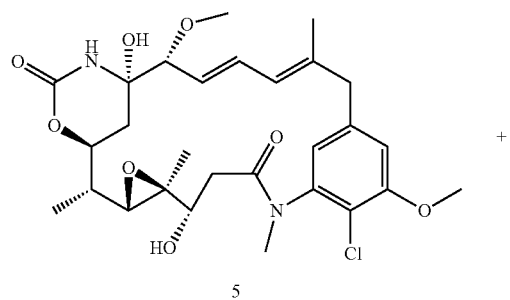

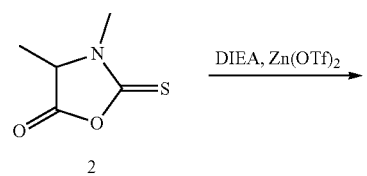

Maytansin-3-N-methyl-L-alanine (compound 6): Maytansinol (compound 5, 45 mg, 0.0796 mmol) was weighed into a dry vial containing a stir flea, treated with a solution of compound 2 (102 mg, 0.703 mmol) in 2-MeTHF (1.2 mL), then with diisopropylethylamine (DIEA, 0.080 mL, 0.459 mmol), zinc triflate (86 mg, 0.237 mmol), and finally dry DMF (0.60 mL). The vial was sealed with a PTFE-lined cap and the reaction stirred at ambient temperature for 20 h. The vial was removed from the glovebox and heated in a sand bath at 50° C. with stirring for another 24 h. The reaction was cooled to ambient temperature, treated with brine, and stirred for 1 h. The crude mixture was extracted thrice with ethyl acetate, the combined organic layers dried over Na$_2$SO$_4$, and filtered over fluted paper. The concentrated filtrate was purified on a 20×20 cm, 1000 um silica gel preparatory plate (eluting with 9:1 dichloromethane/methanol), and the major product band triturated, filtered, and filtrate evaporated and dried in vacuo giving the title compound as a gold solid (11 mg, 21%). Maytansinol is recoverable from this reaction. MS (ESI, pos.): calc'd for $C_{32}H_{44}N_3O_9Cl$, 649.28; found 650.4 (M+H), 672.3 (M+Na). $^1$H-NMR (500 MHz, CDCl$_3$): δ 6.86 (s, 1H), 6.84 (s, 1H), 6.44 (dd, 1H), 6.28 (s, 1H), 6.17 (d, 1H), 5.51 (dd, 1H), 4.97 (d, 1H), 4.27 (t, 1H), 3.99 (s, 3H), 3.85 (s, 1H), 3.49 (m, 3H), 3.41 (m, 1H), 3.36 (s, 3H), 3.20 (m, 2H), 2.86 (m, 2H), 2.58 (m, 1H), 2.49 (br s, 2H), 2.44 (m, 1H), 2.26 (br d, 1H), 1.69 (s, 3H), 1.62 (m, 2H), 1.36-1.26 (m, 10H), 0.85 (s, 3H). Diastereomeric excess of the desired Maytansin-3-N-methyl-L-alanine was determined to be ≥95% based on $^1$H NMR (based on comparison of integration of the H$^1$-NMR peaks at 5.44 ppm (undesired) vs 5.51 ppm (desired) and limit of detection of 5%).

Maytansin-3-N-methyl-L-alanine (compound 6, alternative preparation 1): All weighing and dissolutions were carried out in a glove box, which was backfilled multiple times with inert gas. Maytansinol (compound 5, 28.1 mg, 0.05 mmol) was weighed into a dry vial containing a stir flea, treated with a solution of compound 2 (102 mg, 0.703 mmol, 14 eq.) in dry DMF (0.3-0.5 mL), then with anhydrous diisopropylethylamine (DIEA, 0.052 mL, 39 mg, 0.3 mmol, 6 eq), zinc triflate (127 mg, 0.35 mmol, 7 eq), and finally rinsed with additional amount of dry DMF (0.3-0.5 mL). The vial was sealed with a PTFE-lined cap, removed from the glove box, and the reaction was stirred at 50° C. for 4 h in a preheated oil bath. [Note: The reaction was monitored both by TLC (2% v/v NH$_4$OH+5% v/v MeOH in EtOAc) and LC-MS]. LC-MS analysis of an aliquot of the reaction mixture indicated a 43% conversion to the product mixture along with ca. 50% of compound 3 and some impurity. The reaction was cooled to ambient temperature, treated with brine, and stirred for 1 h. The crude mixture was extracted thrice with ethyl acetate, the combined organic layers dried over Na$_2$SO$_4$, and filtered over fluted paper. The concentrated filtrate was purified on a 20×20 cm, 1000 um silica gel preparatory plate (eluting with 2% NH$_4$OH+6% MeOH in EtOAc), and the desired product band (slow running band) triturated, filtered, and filtrate evaporated and dried in vacuo giving the title compound as a gold solid (12 mg, 21%). Maytansinol and ca. 20% of the other epimer were also recovered from this reaction. MS (ESI, pos.): calc'd for C$_{32}$H$_{44}$N$_3$O$_9$Cl, 649.28; found 650.4 (M+H), 672.3 (M+Na). $^1$H-NMR (500 MHz, CDCl$_3$): δ 6.86 (s, 1H), 6.84 (s, 1H), 6.44 (dd, 1H), 6.28 (s, 1H), 6.17 (d, 1H), 5.51 (dd, 1H), 4.97 (d, 1H), 4.27 (t, 1H), 3.99 (s, 3H), 3.85 (s, 1H), 3.49 (m, 3H), 3.41 (m, 1H), 3.36 (s, 3H), 3.20 (m, 2H), 2.86 (m, 2H), 2.58 (m, 1H), 2.49 (br s, 2H), 2.44 (m, 1H), 2.26 (br d, 1H), 1.69 (s, 3H), 1.62 (m, 2H), 1.36-1.26 (m, 10H), 0.85 (s, 3H). Diastereomeric excess of the desired Maytansin-3-N-methyl-L-alanine was determined to be ≥95% based on $^1$H NMR (based on comparison of integration of the $^1$H-NMR peaks at 5.44 ppm (undesired) vs 5.51 ppm (desired) and limit of detection of 5%). Analytical Data for the other epimer: MS (ESI, pos.): calc'd for C$_{32}$H$_{44}$N$_3$O$_9$Cl, 649.28; found 650.3 (M+H), 672.3 (M+Na). $^1$H-NMR (500 MHz, CDCl$_3$): δ 6.85 (d, 1H), 6.72 (d, 1H), 6.46 (dd, 1H), 6.30 (s, 1H), 6.15 (d, 1H), 5.44 (dd, 1H), 4.82 (dd, 1H), 4.27 (app. t, 1H), 3.99 (app. s, 4H), 3.50 (m, 3H), 3.34 (app. s, 4H), 3.10-3.26 (m, 5H), 3.0 (d, 1H), 2.40-2.60 (m, 4H), 2.23 (dd, 2H), 2.10 (app. s, 1H), 1.40-1.70 (m, 17H), 0.85 (app. s, 3H).

Example 4

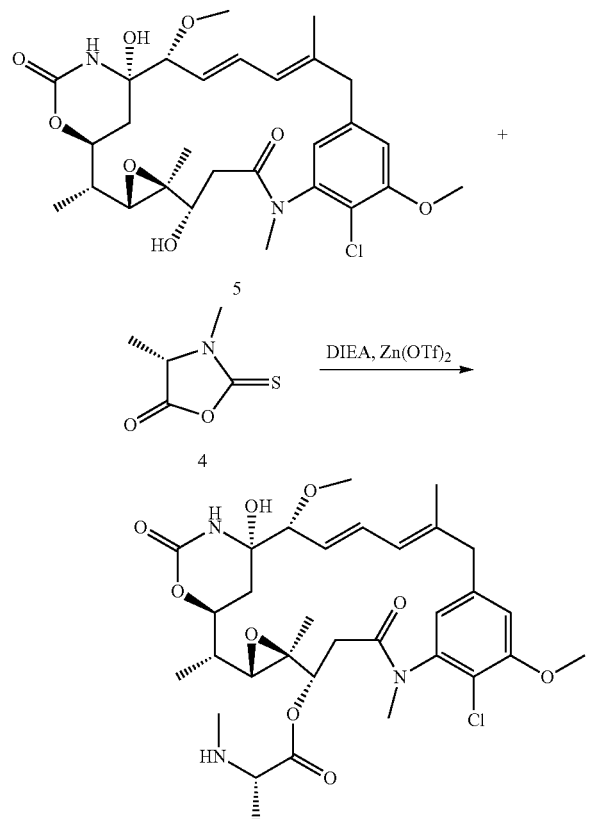

Maytansin-3-N-methyl-L-alanine (compound 6): Maytansinol (compound 5) is reacted with compound 4 in a similar manner to Example 3 to obtain compound 6.

The embodiments and examples described above are intended to be merely illustrative and non-limiting. Those skilled in the art will recognize or will be able to ascertain using no more than routine experimentation, numerous equivalents of specific compounds, materials and procedures. All such equivalents are considered to be within the scope and are encompassed by the appended claims.

We claim:

1. A compound of Formula (I):

wherein:
R$^1$ is methyl, and
R$^2$ is methyl.

2. A compound of Formula (Iaa):

wherein the compound is stereomerically pure.

3. A method of preparing a compound of Formula (II):

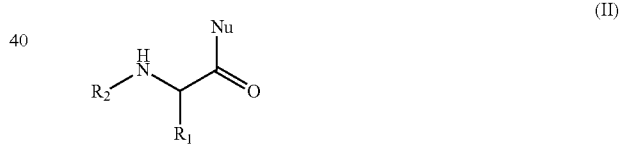

comprising contacting a compound of Formula (I):

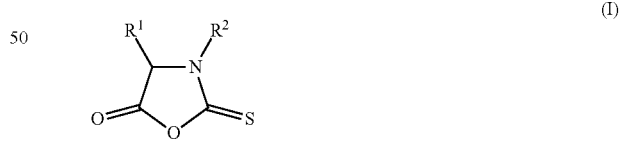

with a nucleophile in the presence of one or more Lewis acids and one or more bases, wherein:
R$^1$ is methyl,
R$^2$ is methyl, and
Nu is an appended portion of the nucleophile,
to form the compound of Formula (II).

4. The method of claim 3, wherein nucleophile is an alcohol.

5. The method of claim 3, wherein the alcohol is a compound having the formula R$^A$—OH, wherein R$^A$ is alkyl, alkenyl, alkynyl, alkaryl, aralkyl, aryl, heteroalkyl, heteroalkenyl, heteroalkynyl, or heterocycloalkyl.

6. The method of claim 3, wherein the nucleophile is a maytansinoid having a C-3 hydroxyl group.

7. The method of claim 3, wherein the nucleophile is a compound of Formula (IV):

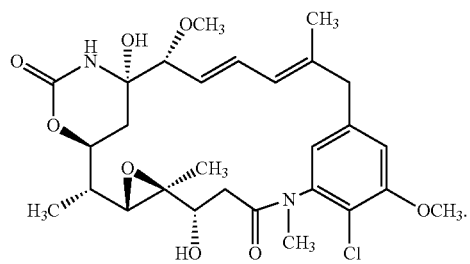

(IV)

8. The method of claim 3, wherein the compound of Formula (II) is a compound of Formula (IIa):

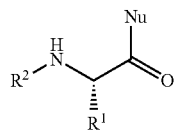

(IIa)

and the compound of Formula (I) is a compound of Formula (Ia):

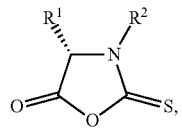

(Ia)

wherein the compounds of Formula (Ia) and (IIa) are stereomerically pure.

9. The method of claim 3, wherein the one or more Lewis acids are selected from the group consisting of Zn(OTf)$_2$, AgOTf, Sc(OTf)$_3$, Cu(OTf)$_2$, Fe(OTf)$_2$, Ni(OTf)$_2$, or Mg(OTf)$_2$.

10. The method of claim 3, wherein the one or more bases are selected from the group consisting of triethylamine, tributylamine, diisopropylethylamine, 1,8-diazabicycloundec-7-ene, and 2,6-di-tert-butylpyridine.

11. The method of claim 3, wherein the method is performed in a diluent comprising one or more polar aprotic solvents selected from the group consisting of diethyl ether, tetrahydrofuran, N,N-dimethylformamide, 2-methyltetrahydrofuran, 1,4-dioxane, and N,N-dimethylacetamide.

12. The method of claim 8, wherein the compound of Formula (Ia) prepared has an enantiomeric excess of at least 95%.

13. A method of preparing a compound of Formula (I) of claim 1:

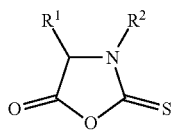

(I)

comprising contacting the a compound of Formula (III):

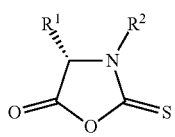

(III)

with 1,1'-thiocarbonyldiimidazole in the presence of one or more bases.

14. The method of claim 13, wherein the compound of Formula (I) is a compound of Formula (Ia):

(Ia)

and the compound of Formula (III) is a compound of Formula (IIIa):

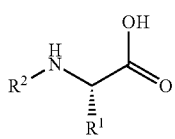

(IIIa)

wherein the compound of Formula (IIIa) is stereomerically pure.

* * * * *